(12) United States Patent
Sheehan et al.

(10) Patent No.: US 10,555,827 B2
(45) Date of Patent: Feb. 11, 2020

(54) MULTIFUNCTIONAL ORTHOSIS DEVICE AND METHOD OF USE

(71) Applicant: FastForm Research Ltd., Waterford (IE)

(72) Inventors: David Sheehan, Dunmore East (IE); David Michael Auerbach, Calabasas, CA (US); Brian P. Casey, Tramore (IE); Brian Murphy, Waterford (IE); Maureen Selina Laverty, Toomebridge (IE); Trevor Kent, New Ross (IE)

(73) Assignee: FastForm Research Ltd., Waterford (IE)

( * ) Notice: Subject to any disclaimer, the term of this patent is extended or adjusted under 35 U.S.C. 154(b) by 949 days.

(21) Appl. No.: 14/965,878

(22) Filed: Dec. 10, 2015

(65) Prior Publication Data

US 2016/0166420 A1 Jun. 16, 2016

Related U.S. Application Data

(60) Provisional application No. 62/091,473, filed on Dec. 12, 2014.

(51) Int. Cl.
*A61F 5/01* (2006.01)
*A61F 5/058* (2006.01)
*A61F 5/30* (2006.01)

(52) U.S. Cl.
CPC ........ *A61F 5/0118* (2013.01); *A61F 5/05866* (2013.01); *A61F 5/30* (2013.01)

(58) Field of Classification Search
CPC ...... A61F 5/0118; A61F 5/05866; A61F 5/30; A61F 5/01; A61F 5/05875; A61F 5/05825

USPC ........ 602/5–7, 16, 20–22, 62; 128/878, 879; 2/16, 21, 158, 159, 160, 163
See application file for complete search history.

(56) References Cited

U.S. PATENT DOCUMENTS

| | | | |
|---|---|---|---|
| 1,615,057 | A | 1/1927 | Emil |
| 3,032,524 | A | 5/1962 | Brewer |
| 3,059,359 | A | 10/1962 | Goldammer et al. |
| 3,375,822 | A | 4/1968 | Rose |
| 3,692,023 | A | 9/1972 | Phillips et al. |

(Continued)

FOREIGN PATENT DOCUMENTS

| | | |
|---|---|---|
| CH | 675963 A5 | 11/1990 |
| DE | 3639717 A1 | 6/1988 |

(Continued)

OTHER PUBLICATIONS

PCT/EP2015/079328 International Search Report and Written Opinion, dated Apr. 1, 2016.

*Primary Examiner* — Ophelia A Hawthorne
*Assistant Examiner* — Caitlin A Carreiro
(74) *Attorney, Agent, or Firm* — Lodestone Legal Group; Jeromye V. Sartain

(57) ABSTRACT

An orthosis device having a substantially rigid thermoformable substrate having a substrate profile defined by a substrate top edge, an opposite substrate bottom edge, and opposite substrate side edges interconnecting the substrate top and bottom edges, the substrate profile being substantially symmetrical about a centerline thereof, whereby the device becomes moldable when activated by a forming temperature above ambient, and the symmetry of the substrate enables the device to be used in both left hand and right hand applications.

24 Claims, 7 Drawing Sheets

Fig. 3

(56) References Cited

U.S. PATENT DOCUMENTS

| | | | |
|---|---|---|---|
| 3,728,206 | A | 4/1973 | Buese |
| 3,906,943 | A | 9/1975 | Arlick |
| 3,985,128 | A | 10/1976 | Garwoord et al. |
| 4,013,798 | A | 3/1977 | Goltsos |
| 4,019,505 | A | 4/1977 | Wartman |
| 4,193,395 | A | 3/1980 | Gruber |
| 4,226,036 | A | 10/1980 | Krug |
| 4,238,522 | A | 12/1980 | Potts |
| 4,240,415 | A | 12/1980 | Wartman |
| 4,273,115 | A | 6/1981 | Holland et al. |
| 4,286,586 | A | 9/1981 | Potts |
| 4,385,024 | A | 5/1983 | Tansill |
| 4,401,113 | A | 8/1983 | Incorvaia |
| 4,411,262 | A | 10/1983 | von Bonin et al. |
| 4,433,680 | A | 2/1984 | Tyoon |
| 4,473,671 | A | 9/1984 | Green |
| 4,502,479 | A | 3/1985 | Garwood et al. |
| 4,537,184 | A | 8/1985 | Williams, Jr. |
| 4,600,618 | A | 7/1986 | Raychok, Jr. |
| 4,609,578 | A | 9/1986 | Reed |
| 4,640,838 | A | 2/1987 | Isakson et al. |
| 4,661,535 | A | 4/1987 | Borroff et al. |
| 4,667,661 | A | 5/1987 | Scholz et al. |
| 4,685,453 | A | 8/1987 | Guignard et al. |
| 4,768,502 | A | 9/1988 | Lee |
| 4,774,937 | A | 10/1988 | Scholz et al. |
| 4,783,917 | A | 11/1988 | Smith et al. |
| 4,802,667 | A | 2/1989 | Altner |
| 4,888,225 | A | 12/1989 | Sandvig et al. |
| 4,946,726 | A | 8/1990 | Sandvig et al. |
| 5,002,212 | A | 3/1991 | Charleton |
| 5,093,176 | A | 3/1992 | Pribonic et al. |
| 5,318,504 | A | 6/1994 | Edenbaum et al. |
| 5,356,371 | A | 10/1994 | Hubbard |
| 5,446,270 | A | 8/1995 | Chamberlain |
| 5,452,930 | A | 9/1995 | Morgan |
| 5,520,621 | A | 5/1996 | Edenbaum et al. |
| 5,547,462 | A | 8/1996 | Lanigan et al. |
| 5,581,810 | A | 12/1996 | Yewer |
| 5,584,800 | A | 12/1996 | Scholz et al. |
| 5,599,283 | A | 2/1997 | Lindenmeyer |
| 5,618,263 | A | 4/1997 | Alivizatos |
| 5,630,959 | A | 5/1997 | Owens |
| 5,652,053 | A | 7/1997 | Liegeois |
| 5,662,596 | A | 9/1997 | Young |
| 5,733,647 | A | 3/1998 | Moore, III et al. |
| 5,752,926 | A | 5/1998 | Larson et al. |
| 5,806,087 | A | 9/1998 | Grotefend |
| 5,807,291 | A | 9/1998 | Larson et al. |
| 5,830,167 | A | 11/1998 | Jung |
| 5,836,902 | A | 11/1998 | Gray |
| 5,979,095 | A | 11/1999 | Schneider et al. |
| 5,980,474 | A | 11/1999 | Darcey |
| 6,055,756 | A | 5/2000 | Aoki |
| 6,074,354 | A | 6/2000 | Scholz et al. |
| 6,093,161 | A | 7/2000 | Vlaeyen et al. |
| 6,098,315 | A | 8/2000 | Hoffmann, III |
| 6,116,666 | A | 9/2000 | Adamson et al. |
| 6,159,877 | A | 12/2000 | Scholz et al. |
| 6,241,567 | B1 | 6/2001 | Evans |
| 6,330,137 | B1 | 12/2001 | Knapp et al. |
| 6,342,540 | B1 | 1/2002 | Gluck et al. |
| 6,547,468 | B2 | 4/2003 | Gruenbacher |
| 6,673,029 | B1 | 1/2004 | Wastson |
| 6,695,801 | B1 | 2/2004 | Toronto et al. |
| 6,880,717 | B1 | 4/2005 | O'Connor |
| 6,903,142 | B1 | 6/2005 | Stauber |
| 6,964,644 | B1 | 11/2005 | Garth |
| 7,201,410 | B1 | 4/2007 | Lassen |
| 7,287,491 | B2 | 10/2007 | Zents et al. |
| 7,438,697 | B2 | 10/2008 | Campagna et al. |
| 7,712,155 | B1 | 5/2010 | Pantoja |
| 7,762,970 | B2 * | 7/2010 | Henderson .......... A61F 5/05866 128/878 |
| 7,895,675 | B2 | 3/2011 | Curphey |
| 7,946,065 | B2 | 5/2011 | Ali et al. |
| 8,375,522 | B2 | 2/2013 | York et al. |
| 8,458,817 | B1 * | 6/2013 | Babb ................. A41D 19/0013 2/159 |
| 2001/0031935 | A1 | 10/2001 | Anderson |
| 2001/0043971 | A1 | 11/2001 | Johns |
| 2001/0044247 | A1 | 11/2001 | Evans |
| 2002/0061690 | A1 | 5/2002 | Evans |
| 2002/0115784 | A1 | 8/2002 | Datko et al. |
| 2002/0143078 | A1 | 10/2002 | Awokola et al. |
| 2003/0098027 | A1 | 5/2003 | Mori |
| 2004/0077979 | A1 | 4/2004 | Karason et al. |
| 2004/0111942 | A1 | 6/2004 | Stonehocker |
| 2004/0133137 | A1 | 7/2004 | Hargis et al. |
| 2004/0194352 | A1 | 10/2004 | Campbell et al. |
| 2004/0210177 | A1 | 10/2004 | Grim et al. |
| 2005/0269318 | A1 | 12/2005 | Zafiroglu et al. |
| 2007/0004993 | A1 | 1/2007 | Coppens et al. |
| 2007/0029314 | A1 | 2/2007 | Rodgers et al. |
| 2007/0218241 | A1 | 9/2007 | Eckerman |
| 2008/0154164 | A1 | 6/2008 | Sheehan et al. |
| 2008/0228120 | A1 * | 9/2008 | Gill ..................... A61F 5/0118 602/22 |
| 2009/0062708 | A1 * | 3/2009 | Padova ................. A61F 5/0118 602/22 |
| 2010/0036300 | A1 * | 2/2010 | Sheehan ............. A61F 5/05825 602/7 |
| 2013/0211304 | A1 * | 8/2013 | Romo ................... A61F 5/0118 602/21 |

FOREIGN PATENT DOCUMENTS

| | | |
|---|---|---|
| EP | 0143348 A1 | 6/1985 |
| EP | 472474 B1 | 1/1996 |
| EP | 0770369 A1 | 5/1997 |
| FR | 2530946 | 3/1984 |
| GB | 2398269 B1 | 1/2006 |
| NL | 1001552 C2 | 5/1997 |
| WO | 1997033541 A1 | 9/1997 |
| WO | 1999020212 A1 | 4/1999 |
| WO | 2005096759 A3 | 10/2005 |
| WO | 2006027763 A2 | 3/2006 |
| WO | 2006077158 A1 | 7/2006 |
| WO | 2008041215 A1 | 4/2008 |

* cited by examiner

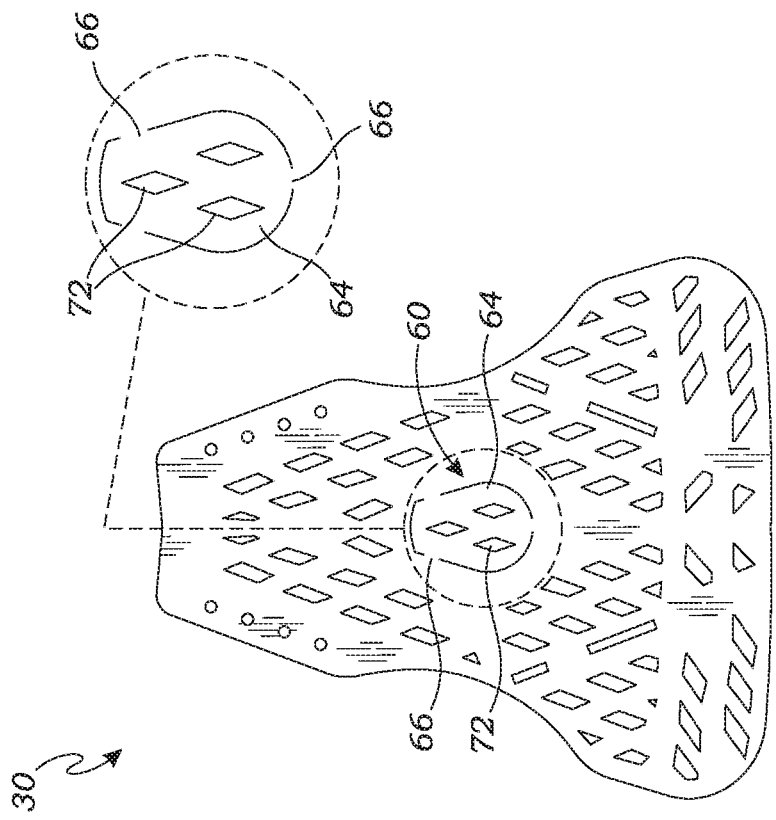
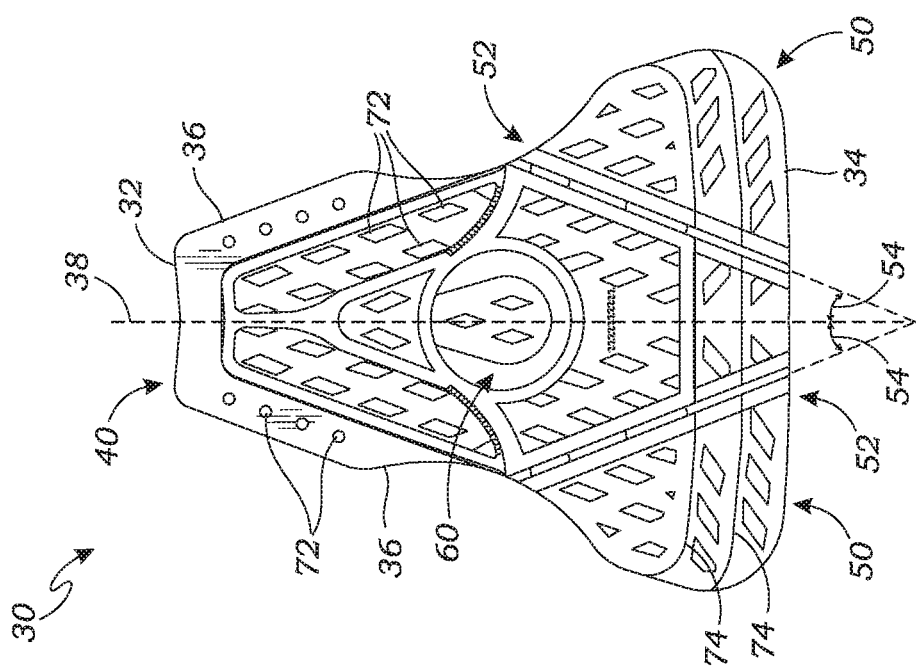
Fig. 4
Fig. 3

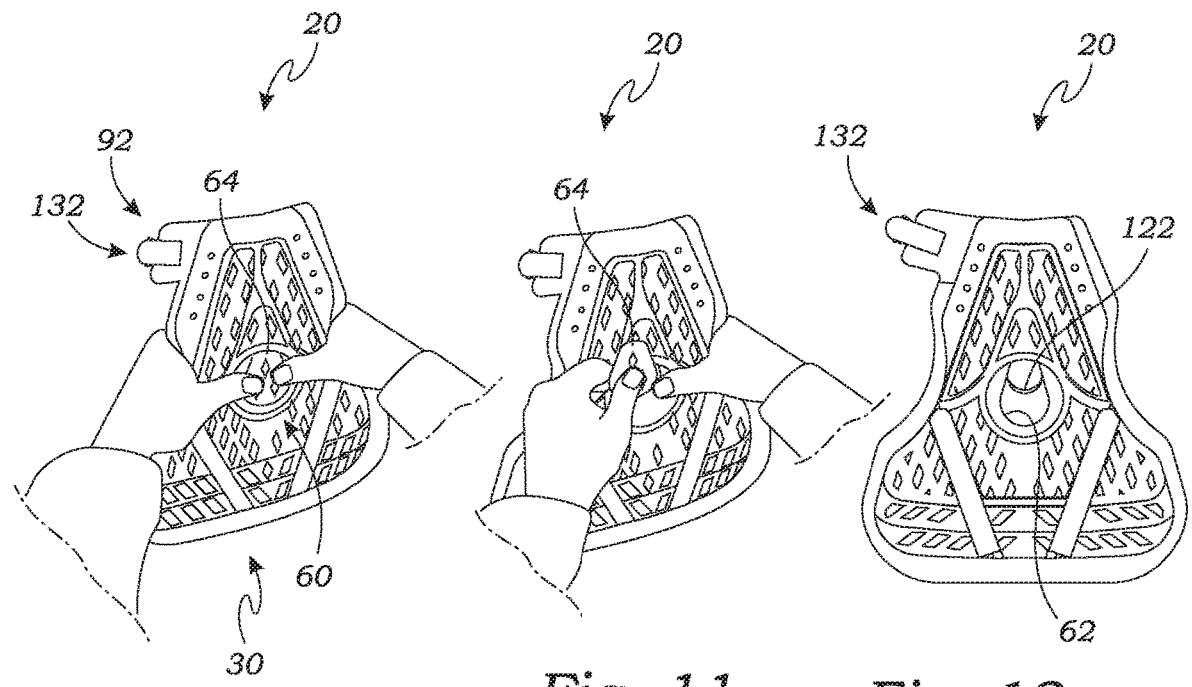
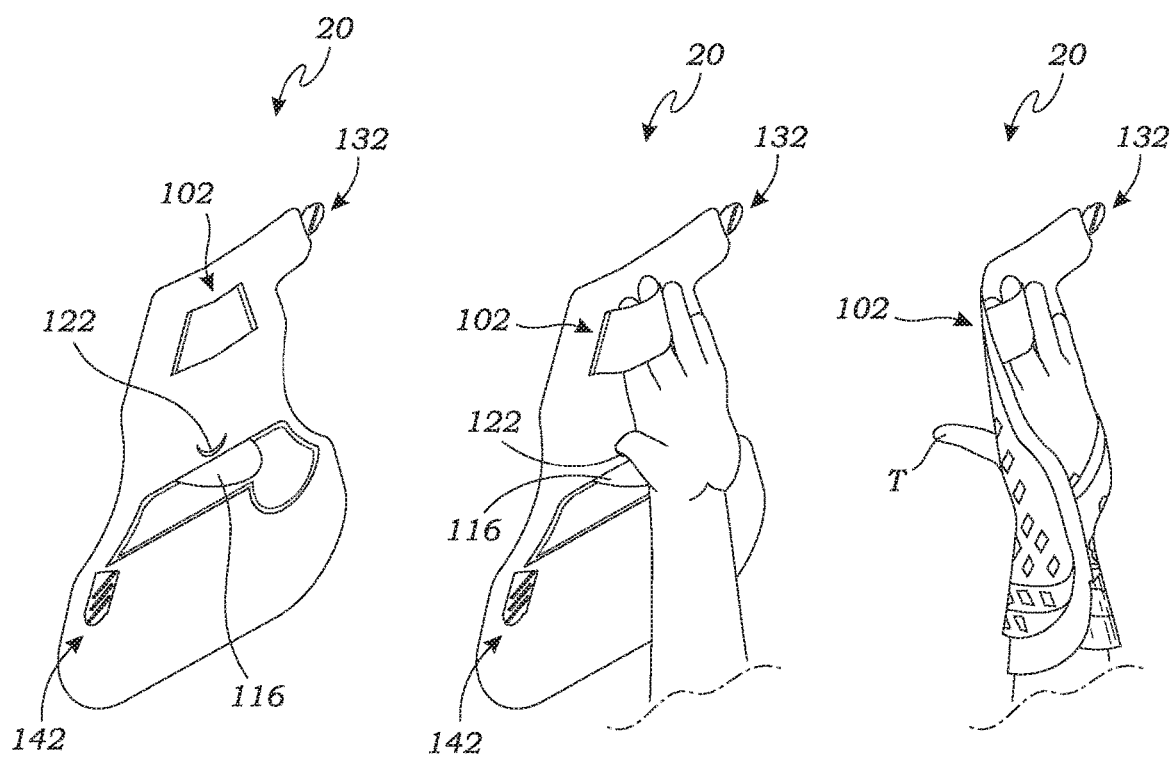

MULTIFUNCTIONAL ORTHOSIS DEVICE AND METHOD OF USE

RELATED APPLICATIONS

This application claims priority and is entitled to the filing date of U.S. provisional application Ser. No. 62/091,473, filed on Dec. 12, 2014 and entitled "Universal Gutter Orthosis Device and Method of Use." The contents of the aforementioned application are incorporated by reference herein.

BACKGROUND

The subject of this patent application relates generally to medical immobilization or orthotic devices, and more particularly to multifunctional orthosis devices and their use.

Applicant(s) hereby incorporate herein by reference any and all patents and published patent applications cited or referred to in this application.

By way of background, immobilization of fractured or injured joints or limbs typically involves the process of restraining the joint or limb in place with a splint, cast, or brace. This is done to prevent the fractured/injured area from moving or being disturbed during the healing process.

Traditionally Plaster of Paris on fabric or gauze bandage has been used to form casts for the immobilization of limbs. However, Plaster of Paris has a number of disadvantages associated with it. For example, Plaster of Paris is relatively heavy and bulky, has a slow setting time, cannot be reformed once set, possesses low impact resistance, and is susceptible to deterioration or damage once exposed to moisture thus making bathing and showering difficult. Additional concerns associated with the use of Plaster of Paris casting bandages are that they require a significant amount of time, usually 24 to 72 hours, to achieve their maximum strength, and that heat is generated from the exothermic setting reaction. Plaster of Paris also has poor radiopacity, which often prevents the continued monitoring of the limb during the healing process. In addition, Plaster of Paris is substantially impervious to transmission of water vapor, such as perspiration. Thus, Plaster of Paris traps moisture, which can result in significant skin maceration.

One partial solution to improve breathability is the use of a thermoplastic mesh as disclosed in U.S. Pat. No. 4,143,655 to Custer et al. A drawback with this method, however, is the necessity to apply multiple layers of mesh to achieve adequate strength to support and protect body areas. Another drawback of this method is that the mesh needs to be trimmed in order to fit different body areas and this results in sharp edges that are formed due to trimming. Another disadvantage of this method is that underlying bandages, padding, dressings, and gauzes can become wet because the material is usually heated using a hot water bath to soften the material to facilitate molding. Moist dressings promote bacteria growth and can lead to discomfort and further complications.

Other proposed solutions involve the use of thermoplastic materials. It is usually prescribed that thermoplastic mesh and thermoplastic sheets with perforations are heated using a water bath. This will help to reduce the (unwanted) high tack characteristic associated with these materials, which makes it otherwise difficult for the user to handle. However, this means that these devices and materials are often wet when applied which can in some instances sustain bacteria growth and MRSA or more generally just be unpleasant for the patient.

In the case of splints and casts it is important that such devices and materials also have sufficient strength to maintain correct alignment of fractured bones, or to restrict movement of a limb in order to promote healing, or to stabilize and help reduce swelling of injured limbs, or to protect a body area from impact and injury. Specifically, in cases where devices or materials are used to protect body parts from impact and injury it is important that the devices or materials have sufficient strength to withstand an impact and also be capable of transmitting/dissipating the force of the impact onto and across underlying padding or shock absorbing materials to reduce or prevent injury to the underlying body part on humans and animals.

Those skilled in the art will recognize the importance of having breathable and open surfaces in devices and materials used for immobilization, bracing, casting, protection, or support of limbs and body parts on humans and animals in order to reduce skin maceration problems and clinical complications and to promote a reduction of healing times while still providing the aforementioned strength and workability and convenience in use.

In the context of hand orthotic devices, so-called "gutter splints" are used to protect, immobilize, and/or cast metacarpal bones and phalanges. Typical metacarpal fractures of the hand on the ulnar side are the 4th and 5th metacarpals, with the 5th metacarpal (little finger) being the most common. As such, the most common gutter splint is nicknamed a "boxer splint" because people often break the 5th metacarpal bone (little finger knuckle) after throwing a punch, or more generally as a result of striking hard object with a fist. The conventional name for a product used to treat this injury to the 5th metacarpal and also the 4th metacarpal bone beside it is an "ulnar gutter." Fractures of the 2nd and 3rd metacarpals on the radial side are less common, hence treatment of the radial side is less common. Radial configuration requires an opening in the gutter splint for the thumb which allows free movement of the thumb while immobilizing the 2nd and 3rd finger. The common name for a product used to treat fractures of the 2nd and 3rd metacarpal bones (fingers next to the thumb) is typically called a "radial gutter."

Traditionally Plaster of Paris or synthetic resin fiberglass have been used to fabricate ulnar gutter splints and radial gutter splints, which materials have the shortcoming noted above. Moreover, the procedure is difficult and requires skill on the part of the plaster technician to make an effective gutter. Furthermore, plaster gutters are generally uncomfortable, heavy and cumbersome, and as indicated above are not breathable or wettable, which may result in itch, odor, and/or discomfort for the patient. In some cases occupational therapists fabricate gutter splints from thermoplastic sheets. This also requires great skill, and both procedures are time consuming. Finally, custom orthotics, which might adequately address some of the concerns regarding functionality or effectiveness, are yet expensive and require additional padding and liner elements which are not usually suitable for exposure to water. Further, conventional custom or pre-formed orthotics and their materials of construction are restrictive for metacarpal fractures and other injuries requiring isolation or need to constrain movement of the fingers, resulting in therapeutic limitations in cases where injuries and rehabilitation regimes require that the fingers are allowed to flex or extend only over a limited range.

More recently, prefabricated thermoplastic devices have been deployed with limited success due to the material configurations chosen and design employed in those devices. These devices can be difficult to mold particularly for position of function and support of the metacarpal heads and have limited breathability due to low surface openness of those devices. That is, fingers are typically molded into a bent position to allow full recovery of flexion/extension post-treatment and such that the knuckles or metacarpal heads are well supported, but the degree of molding that is possible is challenging with the current state of the art materials, particularly with both resin/fiber and pre-cut or prefabricated thermoplastic splints. Furthermore, such prefabricated thermoplastic devices can essentially only be used for a single indication and are not universal (ambidextrous). For example, a discrete prefabricated thermoplastic device product is needed for each of the following:

RH Ulnar Gutter×1
LH Ulnar Gutter×1
RH Radial Gutter×1
LH Radial Gutter×1
Total=4 Discrete devices needed.

Thus, typically with prefabricated thermoplastic devices found in the art, five (5) sizes are needed to cover the population, therefore four product types times five sizes equals twenty (4×5=20) devices needed to cover the general population. This represents added cost and a challenge for inventory management and stocking levels especially for small clinics.

Therefore, currently the market is poorly served with effective product solutions.

The present specification addresses the shortcomings of known orthotic devices particularly in the context of gutter orthotics as might be employed in or as hand gutter splints.

Aspects of the present invention fulfill these needs and provide further related advantages as described in the following summary.

SUMMARY

Aspects of the present invention teach certain benefits in construction and use which give rise to the exemplary advantages described below.

Aspects of the present specification provide for a symmetrical substantially rigid substrate which becomes soft and moldable when activated by temperatures above ambient, which enables the device to be used in both left hand and right hand applications. The combination of the substrate symmetry, the design of the contours and other features allow the device to be used in the treatment of both ulnar and radial injuries.

Other aspects of the present specification provide a double angled hinge that further allows the device to be used in ulnar and radial contexts for both left hand and right hand applications with relatively easy removal and refitting.

Other aspects of the present specification provide a thumb-hole plug that is used to differentiate between radial and ulnar applications and that can easily be configured by the user for radial applications by manually applying pressure to the thumb-hole plug to remove it pre-activation.

Other aspects of the present specification provide for the thumb hole plug to remain in place in ulnar applications of the device, the plug featuring in an illustrated embodiment a raised edge around its perimeter which molds solidly and permanently into the body of the multifunctional splint after activation. Thus, in ulnar applications, the plug will remain in place and in the activation and application process will become integrated with the main splint body.

Other aspects of the present specification provide an "easy close" tab feature as a layered system comprising a hook element attached to the liner fabric and a loop or velour element attached to the hook. The velour element may have a hot melt, pressure sensitive, or other adhesive backing with a peel off release paper. In use, the release paper is removed and the adhesive element applied to the activated polymer substrate at any point on the overlapping surface to define the optimum position of closure. Due to the interaction of the hot melt adhesive and the warm thermoplastic in its active state a strong and robust bond can be achieved between these two elements. In subsequent use, opening and closing of the device in its set condition is achieved by opening and closing the hook and loop fastener(s). This advantageously removes the need to have a large strip of Velcro® hook and loop fastener or the like in a predefined receiving area to fix the loop Velcro® strap as by accounting for the kind of patient variance the device might see. The improved configuration defines its own optimal position for closure of the device based on the individual characteristics of the patient.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings:

FIG. 3 is a front view of a thermo-formable substrate thereof, in accordance with at least one embodiment;

FIG. 4 is a back view of a thermo-formable substrate thereof, in accordance with at least one embodiment;

FIG. 10 is a schematic view thereof illustrating a first operational mode in a second exemplary use of the exemplary multifunctional orthosis device, in accordance with at least one embodiment;

FIG. 11 is a schematic view thereof illustrating a second operational mode in the second exemplary use thereof, in accordance with at least one embodiment;

FIG. 12 is a schematic view thereof illustrating a third operational mode in the second exemplary use thereof, in accordance with at least one embodiment;

FIG. 13 is a schematic view thereof illustrating a fourth operational mode in the second exemplary use thereof, in accordance with at least one embodiment;

FIG. 14 is a schematic view thereof illustrating a fifth operational mode in the second exemplary use thereof, in accordance with at least one embodiment;

FIG. 15 is a schematic view thereof illustrating a sixth operational mode in the second exemplary use thereof, in accordance with at least one embodiment;

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

The present specification discloses a generally symmetrically shaped multifunctional orthosis device with apertures and at least partially formed from re-moldable thermoplastic material that can be used as a composite splint material for immobilization, bracing, casting, protection, or support of limbs and body parts on humans and animals. Besides treating breaks, sprains and other injuries, a device according to aspects of the present invention may find application in treating such other diseases and conditions of the arm, wrist, and/or hand as carpal tunnel syndrome and Dupuytren's contracture. The term "splint" employed herein generally refers to an embodiment of the device in a sheet or a preformed sheet used for limb immobilization, support, and/or protection but is to be understood more broadly as any such stabilization orthotic device in whatever form according to aspects of the present invention, and in any event all such illustrated embodiments herein are to be understood as exemplary and non-limiting.

Figures 1, 2:
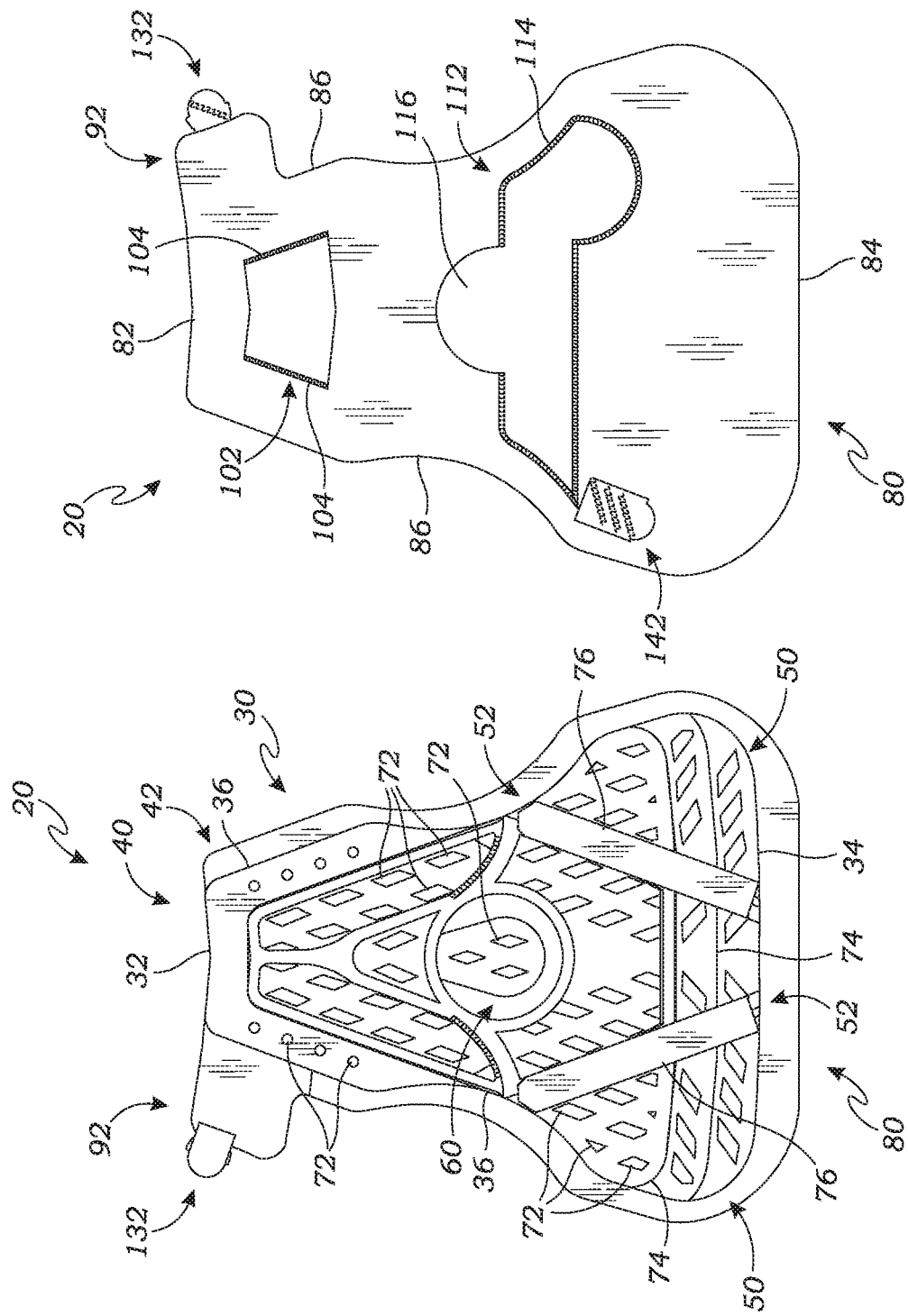
FIG. 1 is a front view of an exemplary multifunctional orthosis device, in accordance with at least one embodiment.
FIG. 2 is a back view thereof, in accordance with at least one embodiment.

As an overview, due to one or more aspects such as the materials technology employed in the present substantially symmetrical multifunctional orthosis device according to aspects thereof, a removable thumb insert plug, and the introduction of two angled hinges in a symmetrical profile designed to function for both ulnar and radial gutter splints, the instant multifunctional orthosis requires essentially only two (2) sizes to cover approximately ninety-five percent (95%) of the population. Therefore, this is a significant improvement or advancement in the state of the art with regard to prefabricated thermoplastic devices, which generally require twenty (20) discrete devices to achieve the same result. This brings significant benefits for clinicians and healthcare professionals by reducing inventory, administration, inventory management and costs. Accordingly, in a bit more detail, aspects of the present invention include:

Low Temperature Thermoplastic
  Open for breathability
  Sufficient strength and stiffness in set condition to support fractures
  Radial and Ulnar side fractures treated with a simple conversion of the unit
  Pop-out thumb hole cover
  Liner flap configured to selectively cover thumb hole or not cover thumb hole in liner
  Left or right hand with a single design
  Configurable for selective isolation of finger flexion or extension over a prescribed limited range
  Easy Closure system which defines its own optimal position
  Reduces requirement for multiple sizes
  Improves the ease of application
  Features a double hinge angled such as to allow easy access for removal and refit in both Ulnar and Radial configurations Turning to FIG. 1, there is shown a front view of an exemplary multifunctional orthosis device 20 according to aspects of the present invention. The device 20 generally comprises a substantially symmetrical thermo-formable substrate 30 and a corresponding liner pad 80, which is itself symmetrical and generally has a similar shape or profile to the substrate 30 except for the outwardly-extending finger wrap tab 92, more about which is said below. The structure of the substrate 30 relative to or as distinct from the liner pad 80 will be further appreciated from the discussion that follows, with particular reference to FIGS. 3 and 4 showing the substrate 30 alone, or apart from the pad 80. In forming the device 20 as shown in FIGS. 1 and 2, the substrate 30 and pad 80 may be attached or otherwise joined together, in whole or in part, in any configuration or manner now known or later developed, including but not limited to any related disclosure in commonly owned U.S. Pat. No. 7,985,192 (the '192 patent), incorporated herein by reference, or employing such techniques as laminating, bonding, adhering, stitching, or the like, whether along an edge or a surface. More particularly, and by way of illustration and not limitation, the substrate 30 may be coupled to the liner pad 80 without the use of an adhesive or any other interfacing coating or material. Specifically, according to aspects of the present invention, the pad 80 may be advantageously coupled (bonded) to the substrate 30 by fusion of the PolyTrexX® substrate polymer to the liner material at the interfacing surfaces when the orthosis device 20 is manufactured, which bond or fusion is enabled by the relative stickiness of the substrate surface when it is heated and somewhat molten as during the manufacturing process. As shown, around one or more sides of the device 20, the perimeter of the pad 80 is configured to extend beyond that of the substrate 30, which it will be appreciated generally and with reference to the below discussion provides extra material to be folded over marginal edges of the substrate 30 for patient comfort, though in the exemplary embodiment the top edge 32 of the substrate 30 is substantially coterminous with the top edge 82 of the liner pad 80. In terms of sizing the device, the substrate 30 is provided across the bottom with one or more trim lines 74, or effectively relatively thinner portions thereof identified or self-evident through the molding process, such trim lines 74 generally being parallel to and offset from the bottom edge 34 of the substrate 30, though it will be appreciated that other arrangements and numbers of such trim lines 74 are possible beyond what is shown, which is merely illustrative. Similarly, and more generally, the overall shapes of both the substrate 30 and the pad 80 are to be understood as merely exemplary and may be varied even in alternative hand gutter splints similar to those illustrated, such as to accommodate more varied or extreme human anatomy or animal anatomy, and certainly in other orthotic or gutter-type devices indicated for other uses while still embodying one or more aspects of the present invention. Accordingly, it will be appreciated by those skilled in the art that the actual and relative sizes, shapes, and configurations of the multifunctional orthosis device 20 and its two main components of the substrate 30 and pad 80 and any features thereof are exemplary and non-limiting, such that a variety of other such orthosis devices may be practiced according to aspects of the present invention without departing from its spirit and scope.

With continued reference to FIG. 1 and as further illustrated in FIG. 3, the thermo-formable substrate 30 is shown as having essentially three portions: a main body portion 40, including an upper stabilizer region 42; opposite lower wing portions 50 coming off of the main body portion 40; and a central portion 60 formed within the main body portion 40. More about each is said below, particularly as to the hinges 52 joining the wing portions 50 to the main body portion 40 and the operation in use of the central portion 60 in connection with the versatility of the device 20. More generally, there is also shown as being formed throughout the substrate 30, and specifically in each of the three portions 40, 50, 60, openings or apertures 72 of various sizes and shapes and spacings relative to one another. It will be appreciated, however, that such apertures 72 need not be formed in each of the portions necessarily, and in some applications may not. Those skilled in the art will appreciate, generally and with further reference to the '192 patent, that such apertures 72 provide for breathability when the device 20 is worn. This may be especially advantageous in the case where the device is employed to splint a part of a patient's body, as in the illustrated embodiment. Therefore, the risk of skin maceration, irritation, and the conditions conducive to bacteria growth are reduced. These openings also allow the device to dry quickly, in the case of splints and casts showering (the device 20 can be washed) and swimming is possible unlike Plaster of Paris and other materials known and used in the art. It will be appreciated that the filler member or liner pad 80 behind the substrate 30 provides further breathability through the apertures 72 as being configured to be located in the one or more openings. Moreover, when the splint device is being used to splint a part of a patient's body, the liner pad 80 or other padding bandage, foam, or spacer member acts to provide a barrier between the splint member and the skin of the patient. Thus, the heat or rigidity of the splint member is prevented from causing discomfort to the patient. In addition, the pad 80 protects the patient's skin in the case where the splint member or substrate 30 is tacky. Consistent with aspects of the present invention and the incorporated disclosures, it will be appreciated that such apertures 72 may vary widely in configuration and location throughout the device 20, such that the pattern shown is to be understood as merely illustrative. As illustrated, the substrate 30 with such apertures 72 effectively is in the form of a mesh with primarily substantially diamond-shaped openings therethrough, which assists with both breathability and workability, namely, enabling the moldable substrate 30 to be easily arranged around an object in a desired location and/or orientation, and to be stretched if necessary. In the case of a splint or cast such as the illustrative multifunctional orthosis device 20 of the present invention, to improve compliance and to facilitate extensibility of the device during molding the diamond mesh may be aligned substantially parallel with the centerline 38 (FIG. 3) of the device 20 and hence of the limb being treated. This design characteristic also allows the system to be used as a full cast, without seam lines. The diamond mesh system also provides excellent shock distribution during impact. In the exemplary embodiment, the mesh may comprise a single uniform flat material with diamond-shaped openings therethrough, the mesh being movable relative to adjoining diamond openings due to the concertina effect and due to stretching of the composite material of the substrate 30 when it is in the flexible configuration. Preferably, the combined effect of movement results in extensibility of up to (plus or minus) 30% in the thermo-formable substrate 30 made from such a composite material and configured with diamond openings/mesh as herein shown and described, though once again this is merely illustrative. In the exemplary embodiment, the substrate 30 is formed as through a molding operation or other such technique now known or later developed in the art and such that the three portions 40, 50, 60 are integral, though it will be appreciated that one or more portions or components may be formed separately and later assembled using any appropriate technique now or later developed, including but not limited to over-molding, bonding, welding, stitching, fusing, adhering, and the like, such as might be the case where particular properties are desired for a select region of the device 20 and so a material other than the primary material of the substrate 30 is to be selected. In such unitary exemplary embodiment of the substrate 30 it is formed of a comparable low-melt thermoplastic polymer formula as disclosed in the '192 patent, which material may be referred to or known by or under the trademark PolyTrexX. More particularly, the composite splint material of or incorporated in whole or in part in the present invention, and again particularly in the substrate 30, may be compounded on conventional equipment, such as two roll mill and extrusion. Likewise, molding may be carried out using compression, transfer, or injection molding and related techniques now known or later developed. Such thermo-formable substrate material may be a radiation, including but not limited to infrared, activated molding article comprising a novel thermoplastic composite, and a technique for producing the same, or may be activated via conventional heating or microwave radiation. On activation, the thermoplastic composite becomes soft and drape-like allowing the user to work the article into the required shape. On cooling, the article forms a rigid splint preserving its shape substantially throughout its lifetime or useful life. Another advantage of this system in relation to conventional splints and casts is its ability to be remolded locally or entirely. This has benefits over conventional splint and cast materials and can be very valuable where the wearer suffers from swelling. Local remolding can be carried out with a hot air gun or a hair dryer.

In more detail regarding the thermo-formable substrate 30 and the exemplary material thereof, the material has a substantially flexible configuration at a forming temperature above ambient temperature and a substantially rigid configuration at ambient temperature, the material generally comprising a low melt polymer and an additive. In one case the low melt polymer comprises a thermoplastic. In another case the low melt polymer comprises a co-polymer. In a further case the low melt polymer comprises a polycaprolactone. In an embodiment, the additive material enhances the mechanical properties of the polycaprolactone. In particular when the composite material is in the flexible configuration at the forming temperature, the additive material provides a degree of bulk to the polycaprolactone which results in a more easy to handle composite material with reduced tackiness. It is thus easier to arrange the flexible composite material in a desired location and/or orientation around an object without the composite material becoming flattened down or compressed. In addition, the additive material may expand upon heating, if required, resulting in a larger cross-sectional area. In this manner the strength-to-weight ratio of the composite material in the flexible configuration and in the rigid configuration is improved. Preferably the material forming temperature is above 40° C. Ideally the material forming temperature is above 50° C. Most preferably the material forming temperature is above 57° C., or is in the range of 60-100° C. In one embodiment the additive material is provided in the form of a plurality of fibers. Preferably the fibers are dispersed throughout the polycaprolactone, which assists in creating a relatively homogenous composite material having substantially uniform properties. By way of illustration and not limitation, one such thermo-formable material and the means for its activation is as disclosed in commonly-owned U.S. Pat. No. 8,853,603 entitled "Thermo-Formable Support Products and Heating Means Therefor," incorporated herein by reference. Those skilled in the art will appreciate that all such material call-outs are illustrative of materials and properties that may be employed in conjunction with and according to aspects of the present invention, but not necessarily and are expressly to be understood as non-limiting.

Turning now to FIG. 2, there is shown the exemplary multifunctional orthosis device 20 of FIG. 1 from the back, so as to see particularly the underside or skin- or patient-facing surfaces and features of the device 20, and the liner pad 80 particularly. As can be seen, a somewhat central padding insert 112 is shown as affixed to the pad 80, such as to provide additional thickness and comfort in affected or potentially protruding areas of the wrist and lower hand. This exemplary internal comfort pad is designed to provide additional padding in the areas of bony prominences both in the radial and ulnar configurations or uses of the device 20. The asymmetric configuration of the padding insert 112 ensures additional comfort that extends to the area of overlap in use. Most notably, the padding insert 112 is shown as being secured around substantially its entire perimeter with stitching 114, except for a thumb hole flap 116, which is not stitched or otherwise affixed to the liner pad 80 so as to be free to move or fold relative to the pad 80 and insert 112, more about which is said below in connection with the device 20 in use. The liner pad 80 also includes an affixed finger sleeve 102 towards the upper end or top edge 82 thereof, the purpose and use of which will also be readily apparent from the below discussion. It is noted as with the padding insert 112 that the finger sleeve 102 is secured to the pad 80 about a portion but not all of its perimeter. Here, the marginal or opposite lengthwise edges are secured again as by stitching 104, leaving the top and bottom or distal and proximal lateral edges unsecured, thereby forming a pocket or sleeve that is open at both ends into which one or more of a wearer's fingers may be inserted during use. It will be appreciated that while both the padding insert 112 and the finger sleeve 92 are described as being secured to the liner pad 80 as by stitching, the invention is not so limited, and any other technique or means for affixing such components together, whether temporarily or permanently, now known or later developed, may be employed, such that sewing or stitching is to be understood as merely illustrative and non-limiting. Regarding the material of the liner pad 80 and its various features, there is generally selected a breathable fabric referred to or known by or under the trademark DermaWick, though it will be appreciated that a variety of such materials now known or later developed may be substituted, in whole or in part. Such preferably breathable fabric may also have wicking properties so as to pull moisture away from the skin and avoid skin maceration, which can again be an issue when wearing a rehabilitation orthosis for extended periods.

With continued reference to FIGS. 1 and 2, there is shown a novel and convenient closure system that complements the structure and operation of the multifunctional orthosis device 20 according to aspects of the present invention. A first "easy close" fastener assembly 132 is shown as being affixed to the finger wrap tab 92 of the liner pad 80 so as to extend substantially laterally therefrom, here attached to the front side of the pad 80. A second such fastener assembly 142 is affixed to the lower half of the pad 80 somewhat adjacent to one of the side edges 86, here shown as being on the back side of the pad 80 and also positioned somewhat adjacent to the padding insert 112. Like the padding insert 112 and the finger sleeve 102, the first and second fastener assemblies 132, 142 may also be affixed to the pad 80 using any assembly technique now known or later developed, including but not limited to stitching, at least for a portion of such assemblies 132, 142. More specifically, it is noted that in the exemplary embodiment the fastener assemblies 132, 142 are configured as hook and loop fasteners also commonly referred to or known by or under the trademark Velcro®, though it will be appreciated that any brand of such hook and loop fasteners may be employed, such that all references to "Velcro" herein should be understood as non-limiting and encompassing any such "hook and loop" type temporary fasteners now known or later developed. Accordingly, one half of the fastener, such as the "hook portion" of each, may be affixed to the pad 80 as above-described and then removably carry the mating "loop portion" of the respective fastener assembly 132, 142. In use, more about which is said below, when the device 20 is rendered flexible as by heating and is then wrapped about the patient's limb, it will be appreciated that the previously unaffixed "loop portion" of each fastener assembly 132, 142 may then be effectively embedded in or otherwise affixed to the malleable substrate 30, just in the right position for the particular patient. Then, when the hardened splint device 20 is to be temporarily removed such as for evaluation or therapy and subsequently replaced, such fastener assemblies 132, 142 being thus positioned within the custom formed device 20 assist in re-securing the device 20 for continued stabilization. Again, more about the operation of the first and second fastener assemblies 132, 142 is said below in connection with the device 20 in various uses. In the exemplary embodiment each "easy close" fastener assembly 132, 142 features a 4-layer system comprising a hook element attached to the liner pad 80, a loop or velour element removably attached to the hook element, a hot melt, pressure sensitive, or other such adhesive backing on the loop element to aid in its securement to the substrate 30 during use, and a peel-off release paper or liner that is removed prior to use. In application, then, the release paper is removed and the adhesive element applied to the activated polymer substrate 30 at any point on the overlapping surface to define the optimum position of closure for the particular patient. Due to the interaction of the hot melt adhesive and the warm thermoplastic in its active state, a strong robust bond can be achieved between these two elements. In use, once more, opening and closing of the device 20 in its set condition is achieved by opening and closing the hook and loop interface. While such a Velcro® fastener system or assembly is thus shown and described, it will be appreciated that any other such mating or engaging, removable or temporary fastener system now known or later developed may be incorporated within the device 20 according to aspects of the present invention without departing from its spirit and scope. That is, any two-part fastening system may be employed according to aspects of the invention by substantially permanently or preliminarily affixing one of the two parts of the system to the pad 80 and having the other part of the fastener temporarily engaged with the first and itself affixed to the substrate 30 during use, as by again being bonded or adhered to and/or embedded in the substrate 30 while in its workable or flexible or activated condition, in which manner the fastener assembly is effectively customized for each patient or use. It will thus be appreciated that such a closure system has broad application beyond the exemplary multifunctional orthosis of the present invention.

Turning now to FIGS. 3 and 4, there are shown front and back views of the thermo-formable substrate 30 alone. With reference first to FIG. 3, the top or front view of the substrate 30, the same features as pointed out previously are readily seen. Notably, there are clearly seen the opposite and substantially angled hinges 52 formed between the main body portion 40 and the wing portions 50 of the substrate 30. It will be appreciated that such hinges may be formed as living hinges as by forming the substrate material relatively thinner in the hinge region, it being understood that a "living hinge" does not contain a pintle and is essentially a portion of an integral material that is relatively thinner or more flexible or is otherwise able to bend relative to adjoining areas of the material so as to mechanically function as a hinge. In addition or instead, the hinges 52 may be effectively formed or rendered operational in use by the liner pad 80 once affixed to the substrate 30 as herein described. Or, instead or in addition, fastener strips 76 (FIG. 1) formed on the front side of the substrate 30 may provide or contribute to such functionality. It will be appreciated by those skilled in the art that any such hinge mechanism or means now known or later developed may be employed in the orthosis device 20 according to aspects of the present invention, alone or in any combination, without departing from its spirit and scope. As shown in FIG. 3, once more, the hinges 52 are substantially symmetrical, here each at substantially the same angle 54 relative to the centerline 38 of the substrate 30. In the exemplary embodiment the angle 54 of each hinge 52 is approximately twenty degrees (20°) to the centerline 38. More generally, relative to the centerline 38 of the product, the range can be from ten to eighty degrees (10-80°), more preferably ten to forty-five degrees (10-45°), and most preferably ten to thirty degrees (10-30°). In use, which will be further appreciated from the below discussion particularly in connection with FIG. 9, the inclusion of the two angled living hinges 52 allows the device to be removed and refitted to the limb with ease and minimal discomfort to the patient, and further along with the symmetrical design of the substrate 30 enable the device 20 to be used in both left hand and right hand applications. Particularly, the enabled movement of the wings 50 relative to the body portion 40 of the substrate, or to positions out of plane relative to the immediate region of the substrate 30, allowed for substantially wide opening of the orthosis device 20 even in the rigid or hardened state of the substrate 30, facilitating removal from and reapplication of the device 20 on the patient. Again, the angled hinges 52 may be covered with velour or other such "loop" material nominally designated as fastener strips 76 (FIG. 1) to act as areas for securing a tensioning strap 160 (FIGS. 8 and 14) or other such stabilizing band in the final configuration. As best shown in FIG. 4, the living hinges 52 are substantially formed between the main body portion 40 and wing portions 50 above or distal of the portions of the substrate 30 above the trim lines 74 (FIG. 3) so as to be substantially unaffected even as the overall length of the device 20 is adjusted in use to suit particular patients. The same is true of particularly the second fastener assembly 142 affixed to the liner pad 80, which will be appreciated from FIG. 2. Ultimately, other such configurations and geometric arrangements are possible in the device 20 according to aspects of the present invention without departing from its spirit and scope. It is noted with respect to the dual angled hinges 52 it was discovered and herein disclosed that the deployment of two angled hinges such as at an angle, for example from ten to thirty degrees (10-30°) from the midline, such that they are not aligned with the centerline 38 of the device 20 from proximal to distal, greatly improves the function of the symmetrically shaped multifunctional orthosis device 20 so as to enable easy opening and closing and removal regardless of whether the device was formed on a right hand (RH) or left hand (LH) ulnar gutter or radial gutter. More generally, by enabling the splint members to move relative to one another, this ensures that the splint device may be adjusted or removed from an object even when the splint members are substantially rigid. Or put another way, by designing the splint device 20 with a series of elements, this ensures that the splint device may be adjusted or removed from the object being splinted even when the splint members are rigid, for example using a hinge system. The hinge system may also be incorporated as part of a laminate system with padding, foaming, or spacer fabrics, as noted above. In one example, the support fabric may act as the hinge for the system. This ensures a complete system, making its application simple and efficient as in the present example of a splint device.

With reference to the back view of the substrate 30 of FIG. 4, there is shown substantially centrally within the central portion 60 a substrate thumb hole cover 64 removably installed or formed within an associated substrate thumb hole 62 (FIG. 12). The removable thumb hole plug or cover 64 is incorporated in the device 20 so as to allow the device 20 to be used for both radial and ulnar applications. The perimeter of the thumb hole cover 64 is separated from the central portion 60 of the device substrate 30 by means of a thin slot, which ultimately defines the thumb hole 62 itself when the plug or cover 64 is selectively removed. Areas of this slot are bridged to form attachment cover tabs 66 that securely carry the plug 64 within the main splint body. As such, the plug or cover 64 is effectively perforated and so can be removed for radial applications of the device 20, as shown and described below in connection with FIGS. 10-17. Whereas, when the substrate 30 is activated and applied by the user to the patient in ulnar applications in which the thumb is not positioned within the device 20, the thumb hole cover 64 remains in place to have a more complete substrate configuration, more about which is said below in connection with FIGS. 5-9. In the exemplary embodiment the thumb hole cover 64 has a raised edge that flows and integrates the cover 64 with the main splint body in the center portion 60, forming a substantially unitary construct, again, in applications such as ulnar splints where the thumb is not affected, though it will be appreciated that even without the raised edge the material may flow somewhat and fuse together when heated and activated. Accordingly, in the illustrated embodiment, the thumb hole plug is molded as an integral part of the main splint body but separated by a thin gap, which gap is bridged in three places with attachment strips to secure the plug to the main splint body until it is to be selectively removed. But it will be appreciated that other such means for removably incorporating such a thumb hole plug or cover 64 beyond those shown and described, and specifically other than the three cover attachment tabs 66 shown, whether in number or configuration, are possible without departing from the spirit and scope of the invention. By way of further illustration and not limitation, the perimeter of the thumb hole cover 64 and thus of the thumb hole 62 itself may be formed as a relatively thinner or recessed area, somewhat akin to flashing in the molding context, or effectively a weakened portion that allows for selective "pop-out" removal of the thumb hole cover 64 without necessarily forming actual slots or slits in the substrate 30 and having one or more bridges or tabs 66 suspending the thumb hole cover 64 within the thumb hole 62. Again, any such configuration allowing for the selective removal of the thumb hole cover 64 is to be understood as being within the spirit and scope of the invention. As also best shown in FIG. 4, including the enlarged inset, even the thumb hole cover 64 may be formed having one or more apertures 72 for breathability of the device 20, particularly again where the device 20 is used in ulnar splint mode wherein the thumb hole cover 64 remains in the substrate 30.

Figures 5, 6, 7, 8, 9:
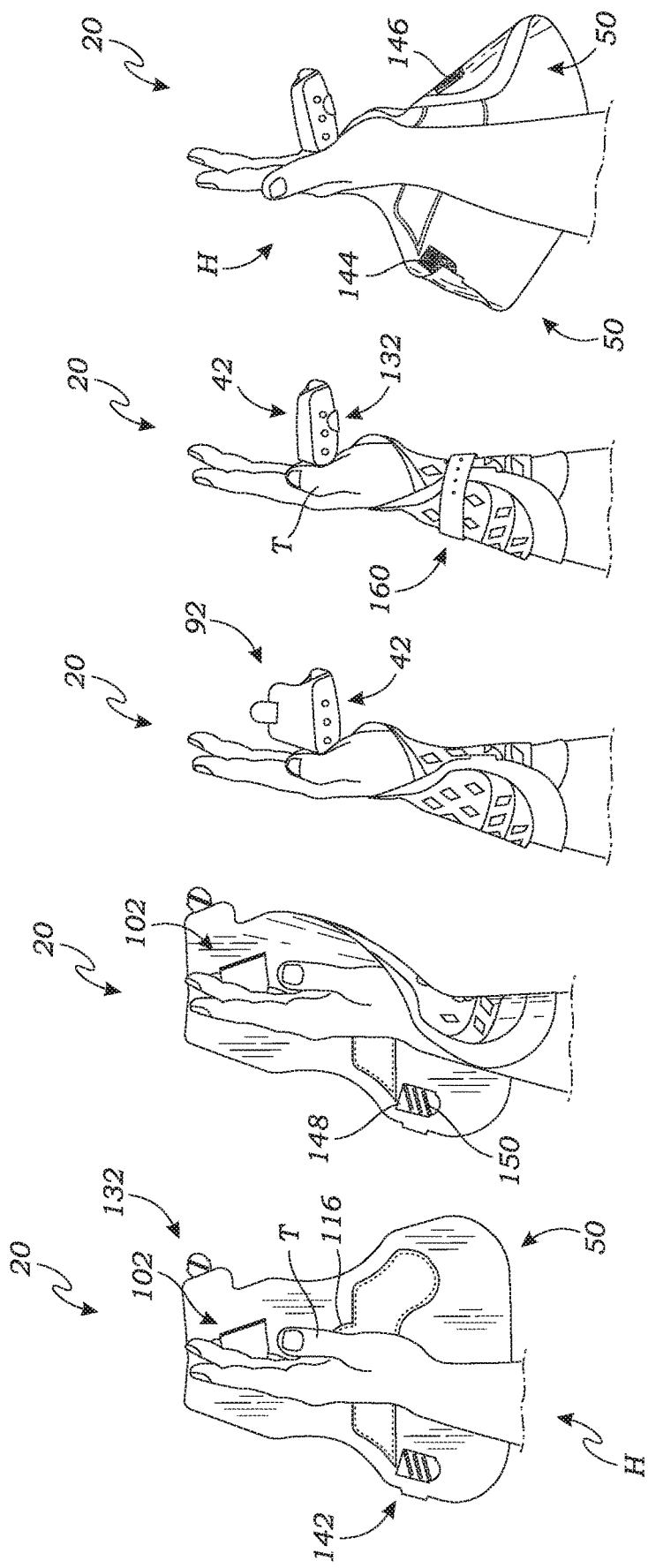
FIG. 5 is a schematic view thereof illustrating a first operational mode in a first exemplary use of the exemplary multifunctional orthosis device, in accordance with at least one embodiment.
FIG. 6 is a schematic view thereof illustrating a second operational mode in the first exemplary use thereof, in accordance with at least one embodiment.
FIG. 7 is a schematic view thereof illustrating a third operational mode in the first exemplary use thereof, in accordance with at least one embodiment.
FIG. 8 is a schematic view thereof illustrating a fourth operational mode in the first exemplary use thereof, in accordance with at least one embodiment.
FIG. 9 is a schematic view thereof illustrating a fifth operational mode in the first exemplary use thereof, in accordance with at least one embodiment.

Turning now to FIGS. 5-9, there are shown perspective schematic views of a multifunctional orthosis device 20 according to aspects of the present invention in various operational modes associated with use of the device 20 as an ulnar splint. Specifically for illustration only, there is shown the device in use in a left hand ulnar splint application. In FIG. 5, the hand H of the patient is slipped into the activated device 20 as by placing the ring and pinky fingers associated with the fourth and fifth metacarpals of the hand H within the finger sleeve 102. As shown by the arrow, the right-hand wing portion 50 from this perspective is to then be lifted and wrapped about the lower arm and wrist area of the affected limb. Then, as shown in FIG. 6, as the device 20 begins to wrap the limb while the hand H remains in the desired position and substantially aligned within the device 20, in part due to the placement of one or more fingers within the finger sleeve 102, in this position, a release liner 150 of the second fastener assembly 142 is removed to reveal the second loop portion 146 (FIG. 9) of the fastener assembly 142, or more particularly the second adhesive element 148 configured to aid in affixing the second loop portion 146 to the opposing activated substrate 30 when the device 20 is fully wrapped about the limb as shown in FIG. 7. As also seen in FIG. 7, once the device 20 is in place, because it is still activated and workable, the stabilizer region 42 at the upper end of the body portion 40 of the substrate 30 and the corresponding portion of the liner pad 80 including the finger wrap tab 92 may then be further conformed to and manipulated to bend the pinky and ring fingers down as clinically advisable, and in any case the finger wrap tab 92 may be wrapped about the one or more fingers that are to be somewhat immobilized as having been previously inserted within the finger sleeve 102 (FIGS. 5 and 6) and held in place when the thermo-formable substrate 30 hardens. It will thus be appreciated that the stabilizer region 42 of the body portion 40 of the substrate 30 in cooperation with the finger sleeve 102 and finger wrap tab 92 of the liner pad 80 of the device 20 function to secure and stabilize the affected or clinically prescribed fingers in use. As with the second fastener assembly 142, the first fastener assembly 132 associated with the finger wrap tab 92 would work on the same basic principle in forming effectively an attachment between the pad 80 and the substrate 30. The device 20 in essentially its final form and then hardened as an ulnar splint is shown in FIG. 8, including an optional strap 160 as may be wrapped around the device 20 to not only further retain the device 20 in place, as by being attached to one or both of the optional fastener strips 76 (FIG. 1), but also providing security or tamper evidence, such as if the patient removed the device 20 without being instructed or authorized to do so. For an example of such a compliance strap, see applicant's U.S. Pat. No. 8,821,423, incorporated herein by reference. Finally, with reference to FIG. 9, in the event that the splint is to be removed from and/or replaced on the affected limb, any compliance strap 160 may be removed, the one or more fastener assemblies 132, 142 operated as appropriate, and the dual hinges 152 selectively operated to open the device 20 relatively widely to accommodate relatively easy removal or reinsertion of the hand H within the device 20. The second hook and loop portions 144, 146 once again further facilitating the re-wrapping and securing of the device 20 about the limb. Though not shown too clearly, it will again be appreciated that in this configuration and use of the multifunctional orthosis device 20 as an ulnar gutter or splint, the thumb not being affected allows for the thumb hole cover 64 to remain in place as above-described. Accordingly, the thumb hole flap 116 remains folded up substantially flat against the liner pad 80, as best shown in FIG. 2, thereby further and substantially completely covering what would be a thumb hole opening 62 in the substrate's central portion 60. It will be further appreciated that the insert padding 112, and particularly the thumb hole flap 116, thus serves to insulate or separate the patient's hand H from the outer substrate 30, which would be somewhat warm or even hot when activated. Thus, the integrated flap 116 on the comfort pad insert 112 prevents potential contact by the patient to the activated polymer substrate 30 during application, eliminating risk of discomfort or burning when the thumb-hole plug 64 is in place for ulnar applications as shown in FIGS. 5-9. Thus, in ulnar applications this section or feature 116 of the comfort pad 112 acts as a protection from the hot PolyTrexX® material that may flow into the thumb-hole cut-out in the fabric liner during application and molding. To summarize according to one exemplary embodiment and use of the device 20 as an ulnar gutter or splint, representative steps in its use would include:

- The device is heated to the appropriate temperature, such as 70-75° C.;
- The device is positioned so that the affected fingers are placed inside the finger sock;
- The device is closed around the wrist and secured by the "easy close" tab;
- The device is closed around the fingers and secured by the "easy close" tab;
- The device is wrapped with a damp Ace wrap to conform the device closely to the contour of the patient's hand, wrist and fingers;
- The clinician then positions the fingers in the correct functional position recommended for treatment of the underlying injury; and
- When the device is rigid the Ace wrap is removed and a D-loop hook and loop strap or the like is tensioned and affixed around the wrist area of the device to maintain a snug fit.

It will again be appreciated that other such steps may be employed as needed and to suit particular contexts without departing from the spirit and scope of the invention. It will also be appreciated that the included finger sock 102 allows potential separation of phalanges or the strapping of two phalanges together during treatment. The finger sock or sleeve 102 also aids the ease of application of the device 20 and acts as a primary datum for ulnar applications and as a secondary datum for radial applications (the thumb-hole being the primary datum in radial applications, as discussed below). The device 20 again features an "easy close system" that uses a method of fixation which is customizable to the individual requirements of each patient as defined by the healthcare professional. In the phalanges area the device 20 is again closed by wrapping the velour backed liner 80 around the fingers to encompass the phalanges to be restricted in movement. The velour adds a comfortable finish to the sensitive area between the fingers. The liner 80 has an assembly where the velour tab is carried on the hook Velcro® or other such component to allow the user to define the appropriate closing location for individual patients. This system allows the phalanges to be supported in the gutter and the compliance tension is created using the stretchable fabric to maintain the phalanges in the correct position. The velour finish creates a comfortable tactile surface for adjacent phalanges during movement of the limb. Similarly, in the wrist area the gutter is closed by wrapping the overlapping areas around the wrist ensuring that the side carrying the Velcro® or other fixation features is located on the top of the construct so as to bond to the substrate 30 as above-described. It will be further appreciated that the incorporation of "velour" or other such material, if at all, as a backing material is optional and merely illustrative of embodiments according to aspects of the present invention and non-limiting.

Figures 16, 17:
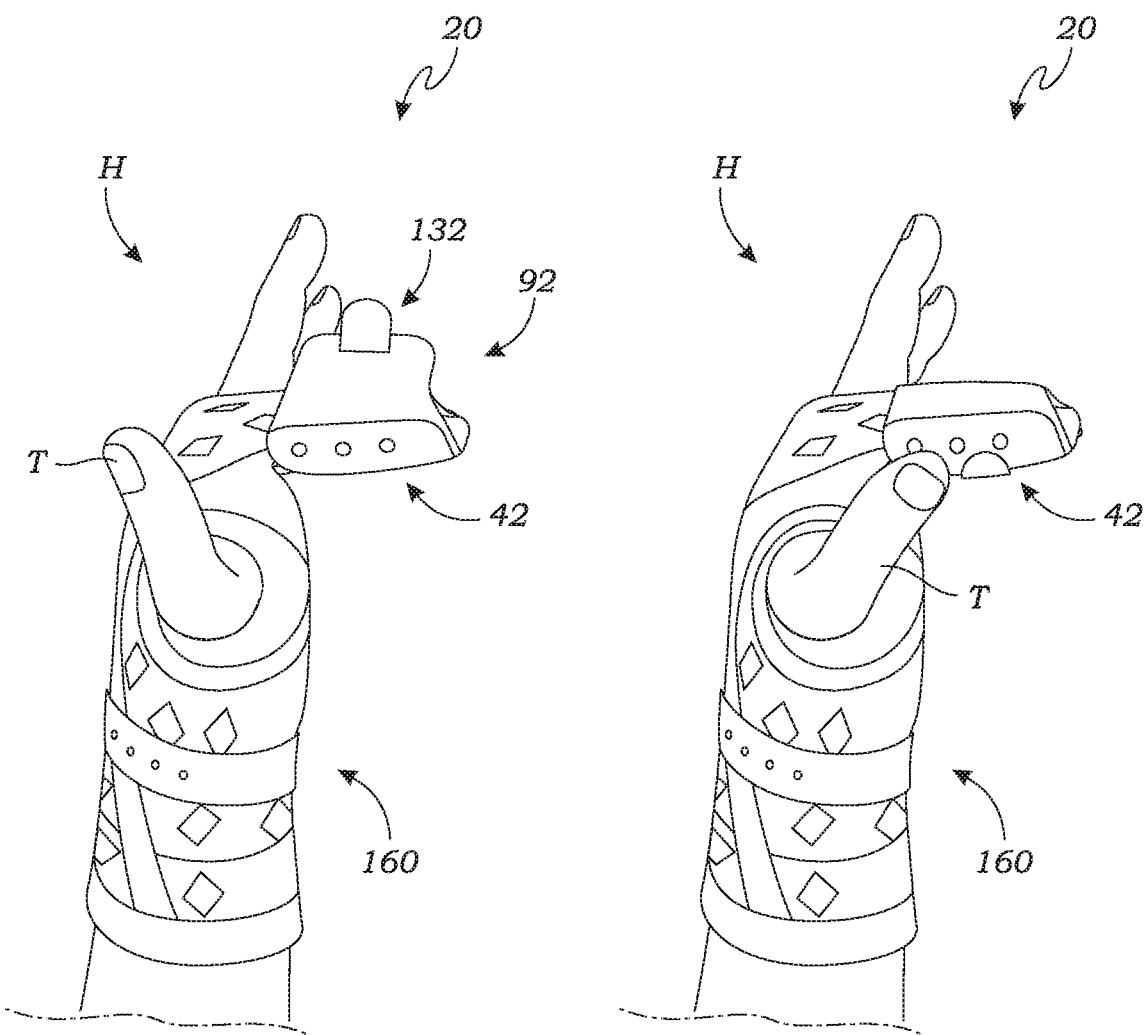
FIG. 16 is a schematic view thereof illustrating a seventh operational mode in the second exemplary use thereof, in accordance with at least one embodiment.
FIG. 17 is a schematic view thereof illustrating an eighth operational mode in the second exemplary use thereof, in accordance with at least one embodiment.

Referring next to FIGS. 10-17, there are shown various views of the multifunctional orthosis device 20 according to aspects of the present invention in various operational modes associated with use of the device 20 as a radial splint. First, as shown in FIGS. 10 and 11, before applying the device 20 to the affected limb and preferably before activating the device 20, the thumb hole cover 64 is removed from the device 20, and specifically the central portion 60 of the substrate 30, as by applying pressure, with one or both thumbs or fingers or through other means, to the thumb hole cover 64 until it is popped out as shown, essentially by overcoming and causing to fail the one or more cover tabs 66 (FIG. 4) originally holding the thumb hole cover 64 in place. Once the thumb hole cover 64 is removed, as shown in FIG. 12, there remains or is opened up the actual substrate thumb hole 62, through which can be seen the liner pad 80 beneath, and particularly the pad thumb hole 122 formed therein and substantially aligned with the substrate thumb hole 62. The device 20 so configured can be activated generally as herein described, and looking then at the back side of the device 20 as shown in FIG. 13, the device 20 so configured and activated can be further prepped for application to the patient's limb by folding down the thumb hole flap 116 to expose the pad thumb hole 122 from the back side, through which the patient's thumb T (FIG. 16) would then be inserted as basically a first installation step. Before or after as generally described above the fastener assemblies 132, 142 may also be prepared for their mating elements to be affixed to the activated substrate as by optionally removing any release liners, for example. Referring next to FIG. 14, there is shown a patient's hand H laid on the open, substantially flat device 20 prepped as above-described. While the left hand is shown, it will again be appreciated that due to the symmetry of the device 20, and particularly the substrate 30, the right hand may be immobilized in the device 20 in a radial splint mode in much the same way. As the thumb T (FIG. 16) is passed through the respective thumb holes 62, 122, the affected finger(s) are also slid into the finger sleeve 102 in a manner similar to that described above for the ulnar splint application, only here being the index and middle fingers associated with the second and third metacarpals most likely, as shown, and the thumb in the thumb holes 62, 122 providing the primary indexing or alignment function. It will be appreciated that in some applications it will be appropriate to only position the index or "pointer" finger in the finger sleeve 102, for example. As shown in FIGS. 15 and 16 generally from below and above, the device 20 is then wrapped about the limb, the hand H and fingers manipulated and the device worked and shaped as needed, and then further secured in place once hardened as with a compliance or retention strap 160 as shown in FIG. 17. Particularly, it is noted as best shown in FIGS. 16 and 17 that once the device 20 is in place, because it is still activated and workable, the stabilizer region 42 at the upper end of the body portion 40 of the substrate 30 and the corresponding portion of the liner pad 80 including the finger wrap tab 92 may then be further conformed to and manipulated to bend the index and middle fingers down as clinically advisable, and in any case the finger wrap tab 92 may be wrapped about the one or more fingers that are to be somewhat immobilized as having been previously inserted within the finger sleeve 102 (FIGS. 14 and 15) and held in place when the thermoformable substrate 30 hardens. It will thus again be appreciated that the stabilizer region 42 of the body portion 40 of the substrate 30 in cooperation with the finger sleeve 102 and finger wrap tab 92 of the liner pad 80 of the device 20 function to secure and stabilize the affected or clinically prescribed fingers in use. As shown best in FIG. 17 with the device 20 in essentially its final form and then hardened as a radial splint, the thumb T is then protruding from the device 20 through the substrate and pad thumb holes 62, 122 (FIG. 12). It will be appreciated once again that various other configurations and adapted uses are possible according to aspects of the present invention. But to summarize regarding the optional radial gutter or splint mode of the device 20, the steps in its use can be generally characterized as:

The thumb hole plug is removed from the device;
The device is heated to the appropriate temperature, such as 70-75° C.;
The device is positioned by fitting the thumb through the thumb hole and also ensuring that the affected finger(s) are placed inside the finger sock;
The device is closed around the wrist and secured by the "easy close" tab;
The device is closed around the fingers and secured by the "easy close" tab;
The device is wrapped with a damp Ace wrap to conform the device closely to the contour of the patient's hand, wrist and fingers;
The clinician then positions the fingers in the correct functional position recommended for treatment of the underlying injury; and
When the device is rigid the Ace wrap is removed and a D-loop hook and loop strap or the like is tensioned and affixed around the wrist area of the device to maintain a snug fit.

Figure 19:
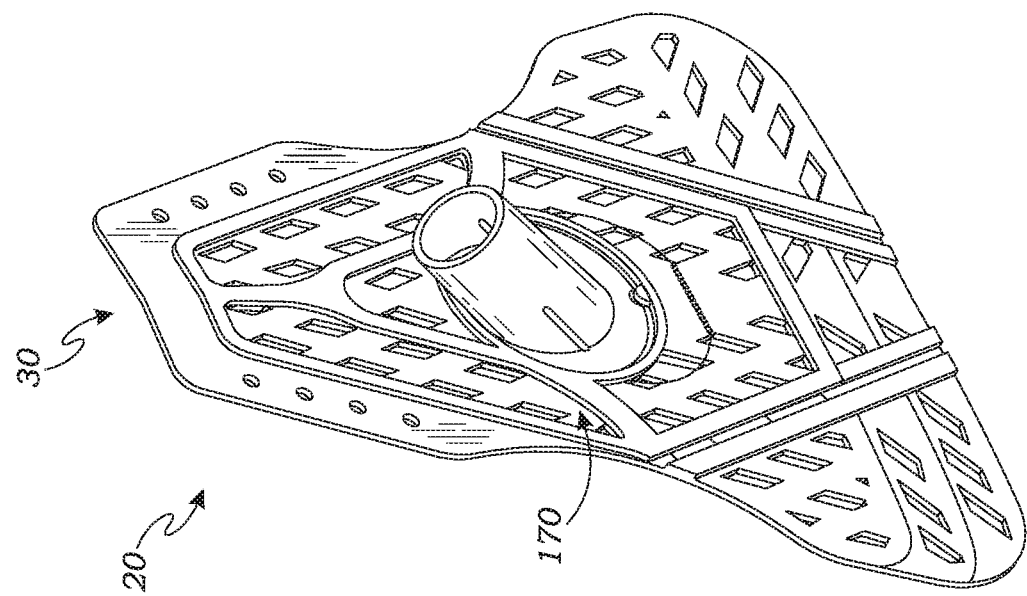
FIG. 19 is a perspective view thereof, in accordance with at least one embodiment.
Figure 18:
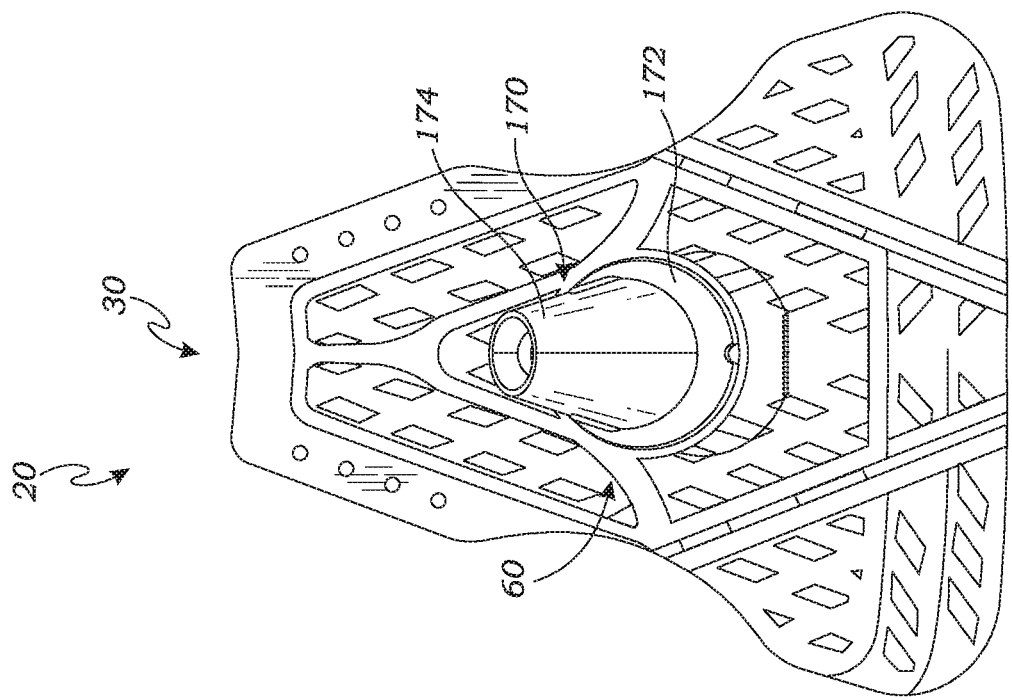
FIG. 18 is a front view of an alternative exemplary thermo-formable substrate of a multifunctional orthosis device, in accordance with at least one embodiment.

It will be appreciated that there is added comfort when the thumb is pushed through the pad thumb hole 122 with the device 20 in such a radial configuration. For this reason, again, the comfort insert pad 112 is not sewn or fixed to the underlying liner 80 in the area of the pad thumb hole 122, thereby allowing the flap 116 to fold back and expose the hole 122 while adding further padding around the thumb at the same time. Briefly referring to FIGS. 18 and 19, there is shown for radial splint applications an optional thumb spica device 170 having a base 172 configured to seat on the central portion 60 of the substrate 30 with an extension 174 protruding at an angle therefrom and formed from a substantially rigid material and configured so as to substantially immobilize the thumb, as in a case where the thumb and one or more metacarpals of the patient were affected. It will be appreciated that other such additional components and features may be employed in conjunction with the multifunctional orthosis device 20 without departing from the spirit and scope of the invention.

As noted previously and will be appreciated from the foregoing, the geometry of the device is symmetrical generally and on the substrate specifically thereby allowing the device to beneficially be used in left hand and right hand and radial and ulnar applications in further view of the selectively openable thumb hole. As such, the exemplary multifunctional orthosis device 20 is operable or configurable to immobilize or support at least the following:

- Right Hand $2^{nd}$, $3^{rd}$ metacarpal phalangeal joint MCP, in flexion and extension
- Right Hand $2^{nd}$, $3^{rd}$, $4^{th}$ metacarpal phalangeal joint MCP, in flexion and extension
- Right Hand $4^{th}$, $5^{th}$ metacarpal phalangeal joint MCP, in flexion and extension
- Right Hand $3^{rd}$, $4^{th}$, $5^{th}$ metacarpal phalangeal joint MCP, in flexion and extension
- Right Hand $2^{nd}$, $3^{rd}$ metacarpal phalangeal joint MCP, in flexion only
- Right Hand $2^{nd}$, $3^{rd}$, $4^{th}$ metacarpal phalangeal joint MCP, in flexion only
- Right Hand $4^{th}$, $5^{th}$ metacarpal phalangeal joint MCP, in flexion only
- Right Hand $3^{rd}$, $4^{th}$, $5^{th}$ metacarpal phalangeal joint MCP, in flexion only
- Right Hand $2^{nd}$, $3^{rd}$ metacarpal phalangeal joint MCP, in extension only
- Right Hand $2^{nd}$, $3^{rd}$, $4^{th}$ metacarpal phalangeal joint MCP, in extension only
- Right Hand $4^{th}$, $5^{th}$ metacarpal phalangeal joint MCP, in extension only
- Right Hand $3^{rd}$, $4^{th}$, $5^{th}$ metacarpal phalangeal joint MCP, in extension only
- Left Hand $2^{nd}$, $3^{rd}$ metacarpal phalangeal joint MCP, in flexion and extension
- Left Hand $2^{nd}$, $3^{rd}$, $4^{th}$ metacarpal phalangeal joint MCP, in flexion and extension
- Left Hand $4^{th}$, $5^{th}$ metacarpal phalangeal joint MCP, in flexion and extension
- Left Hand $3^{rd}$, $4^{th}$, $5^{th}$ metacarpal phalangeal joint MCP, in flexion and extension
- Left Hand $2^{nd}$, $3^{rd}$ metacarpal phalangeal joint MCP, in flexion only
- Left Hand $2^{nd}$, $3^{rd}$, $4^{th}$ metacarpal phalangeal joint MCP, in flexion only
- Left Hand $4^{th}$, $5^{th}$ metacarpal phalangeal joint MCP, in flexion only
- Left Hand $3^{rd}$, $4^{th}$, $5^{th}$ metacarpal phalangeal joint MCP, in flexion only
- Left Hand $2^{nd}$, $3^{rd}$ metacarpal phalangeal joint MCP, in extension only
- Left Hand $2^{nd}$, $3^{rd}$, $4^{th}$ metacarpal phalangeal joint MCP, in extension only
- Left Hand $4^{th}$, $5^{th}$ metacarpal phalangeal joint MCP, in extension only
- Left Hand $3^{rd}$, $4^{th}$, $5^{th}$ metacarpal phalangeal joint MCP, in extension only Any such applications would be as clinically indicated and may beneficially be achieved by the single device 20 according to aspects of the present invention, excepting size ranges that may still be provided. Within any such size ranges, other adjustments may again be made as by trimming the device to adjust its overall length as deemed appropriate for individual patients by the healthcare professional. The gutter section of the device used to support the phalanges can also be trimmed in length and width to create a one sided support allowing movement in either flexion or extension. Furthermore, application areas of the device include or may be extended to braces, splinting fixation and casting bandaging for orthopaedic applications, custom molded seating, handles and grips, degradable cutlery, protective padding such as shin guards for humans or animals, foot orthotics, braces and supports for ulcerated foot conditions, hip protectors, etc.

Figure 20:
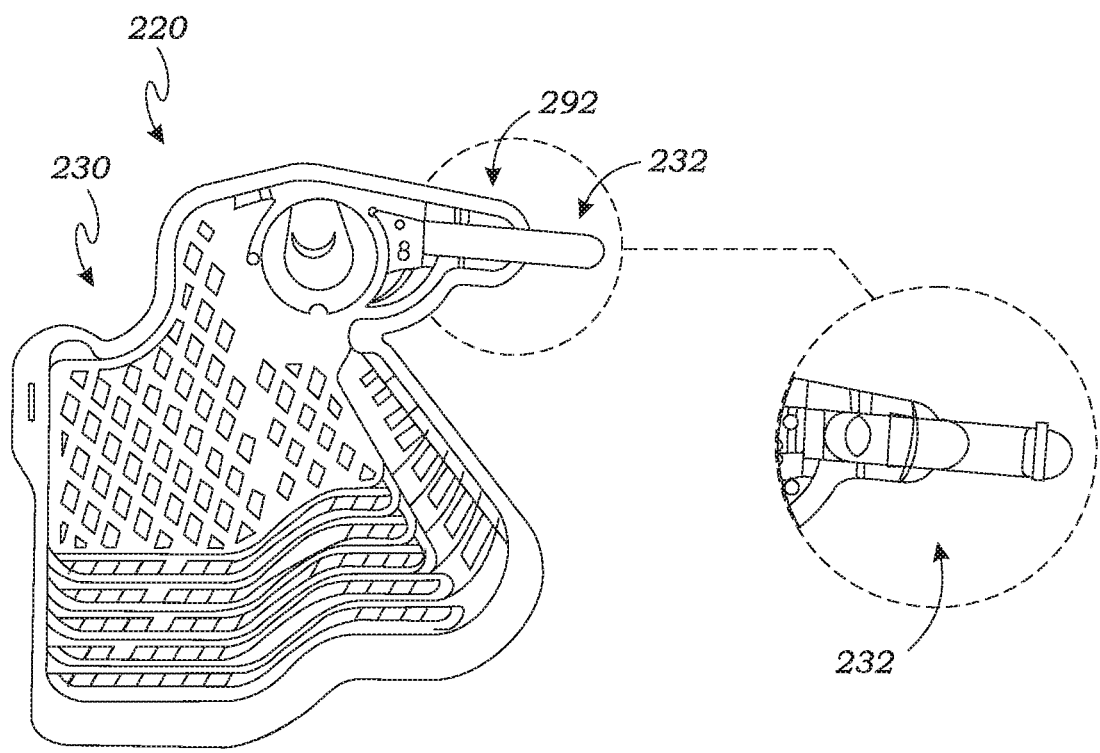
FIG. 20 is a front view of a further alternative exemplary orthosis device, in accordance with at least one embodiment.
Figure 21:
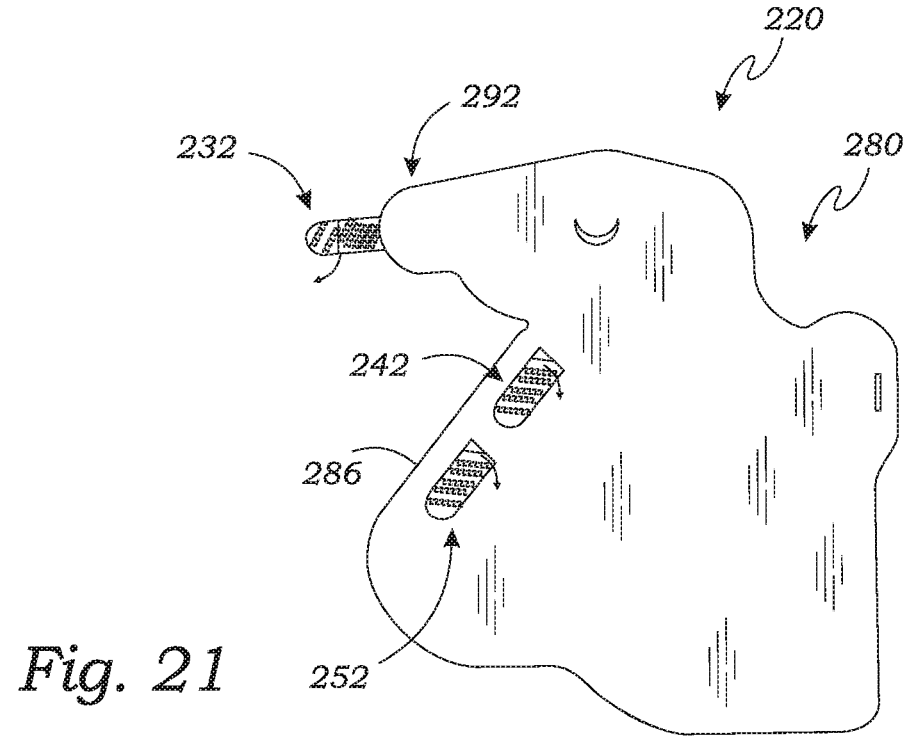
FIG. 21 is a back view thereof, in accordance with at least one embodiment.

Briefly, FIGS. 20 and 21 illustrate a further alternative exemplary embodiment according to aspects of the present invention wherein at least one "easy close" fastener assembly is incorporated within an orthosis device 220. Here, there are shown three such fastener assemblies, a first fastener assembly 232 on or adjacent an upper tab 292 of the device 220, here shown as attached directly to one point on the substrate 230, and second and third fastener assemblies 242, 252 positioned on the back side of the device's liner pad 280 substantially aligned along a side edge 286 thereof. It will be appreciated that a variety of other numbers, configurations, and placements of such "easy close" fastener assemblies may be incorporated in an array of splint or orthosis devices 220 according to aspects of the present invention, such that this further exemplary embodiment is to be understood as illustrative and non-limiting. Particularly, while the illustrated orthosis device 220 of FIGS. 20 and 21 is shown as somewhat unsymmetrical as to suit a particular left hand or right hand application, it will be appreciated that the device may also be configured to be symmetrical as in other exemplary embodiments illustrated herein, or the illustrated type, number, and position of such "easy close" fastener assemblies may be embodied in other device configurations as illustrated herein or otherwise. Fundamentally, those skilled in the art will appreciate that all such features as disclosed herein, including but not limited to the shape or profile of the device, and the thermo-formable substrate specifically, the incorporation and configuration of any hinged wing portion, the incorporation and configuration of any central or offset portion having a thumb hole with or without a pop-out thumb hole cover, and the incorporation of one or more fastener assemblies, may be combined in a virtually infinite variety of ways according to aspects of the present invention without departing from its spirit and scope.

EXAMPLES

The following non-limiting examples are provided for illustrative purposes only in order to facilitate a more complete understanding of representative embodiments now contemplated. These examples are intended to be a mere subset of all possible contexts in which the device 20 may be utilized. Thus, these examples should not be construed to limit any of the embodiments described in the present specification, including those pertaining to multifunctional orthosis devices and/or methods and uses thereof. Ultimately, the device 20 may be utilized in virtually any context where immobilization or protection is desired.

Example 1

Fracture Management

A patient was treated in the doctor's office for a non-displaced metacarpal fracture of the left hand. Typically these are treated in an ulnar gutter cast. Typically the patient returns for multiple visits for cast removal, repeat x-rays, and then reapplication of a new cast. Once the bone is healed the patient typically goes into a removable gutter brace until they have regained their motion and strength and no longer need protection. The present patient was treated with a thermo-formable multifunctional orthosis device instead, capable of being used in left hand and right hand applications. The device was formed after activation and then allowed to harden and at first was made non-removable with use of a Velcro® strap locking mechanism. For the patient's return visits the device was easily removed, x-rays taken, and then the patient placed back into the device, which could be remolded as necessary as by re-activation. Once the bone was healed, the device was used in a removable fashion until the patient no longer needed protection for the healed fracture. Rather than the patient using multiple casts, which would need to be cut off each time, and then having to use a different removable brace, this patient was able to use the same multifunctional orthosis device for the entire duration of the patient's fracture management, reducing the doctor's office inventory both of traditional cast and brace supplies and even of multifunctional orthosis devices since one device can advantageously be used for such applications on either the right or left hand.

Example 2

Maintaining Fracture Reduction

A patient had a displaced metacarpal neck fracture otherwise known as a boxer's fracture in the right hand. Typically the fracture is reduced and held in position by a plaster cast. A plaster cast is often used as plaster is a good molding material and can be applied to maintain pressure on the fracture fragment to prevent it from displacing until early healing has occurred. Plaster casts however are relatively heavy and difficult to apply, which may need to be repeated multiple times for follow-up evaluation. And once early healing has occurred the plaster cast is usually exchanged for a removable brace until complete healing of the fracture has occurred. The present patient instead had the fracture reduced and held in position with a multifunctional orthosis device. Because of the moldability of the thermo-formable material of the device, the fracture was held in position with molding just as effectively as with a plaster cast, while unlike a traditional cast the device is lighter weight and waterproof as well as being easily removed for evaluation and then reapplied. The fracture was maintained in good position by the device and then once fracture healing had occurred, the device was used as a removable brace until protection was no longer necessary.

Example 3

Pre- and Post-Operative Management

A patient had a left hand metacarpal fracture requiring surgical fixation with plate and screws. Typically the patient is placed in a bulky bandage and plaster splint in the operating room after the surgery to protect the fixed bone until the first post-operative visit at which time a removable brace would be applied. This requires the use of plaster in the operating room which is cumbersome and messy. Instead, prior to surgery the patient had applied a multifunctional orthosis device for protection and comfort. After the surgery was completed and while still in the operating room, rather than applying a plaster splint over a bulky bandage, the patient's same multifunctional orthosis device was remolded using the conduction oven in the operating facility, and the device was reapplied over a light bandage. One week later in the office the same orthosis device was reheated and remolded as necessary to fit the patient after reduced swelling and after the bandage was no longer necessary. This same device was then used until the bone had healed, advantageously completely obviating the need for multiple removable braces and post-operative plaster and reducing the hospital inventory both of traditional cast and brace supplies and even of multifunctional orthosis devices, as needed, since one device can advantageously be used for such applications on either the right or left hand.

Example 4

Fracture Management

A patient presented with a somewhat rare fracture of the 2nd metacarpal in the right hand as determined in a doctor's office evaluation. Such "radial side" injuries and their treatment being less common, typically these are treated in a radial gutter cast. Typically the patient returns for multiple visits for cast removal, repeat x-rays, and then reapplication of a new cast. Once the bone is healed the patient typically goes into a removable radial gutter brace until they have regained their motion and strength and no longer need protection. The present patient was instead treated with a thermo-formable multifunctional orthosis device capable of being used in left hand and right hand applications and in radial and ulnar applications as well. Prior to activation, the pop-out thumb hole cover formed in the device's substrate was removed and the thumb hole flap on the plush liner pad was pushed through the thumb hole for added patient comfort. The device was then activated and formed, including passing the patient's right thumb through the thumb hole and shaping the device as needed on the patient's right hand and allowed to harden. For the patient's return visits the device was easily removed, x-rays taken, and then the patient placed back into the device, which could be remolded as necessary as by re-activation. Once the bone was healed, the device was used in a removable fashion until the patient no longer needed protection for the healed fracture. Rather than the patient using multiple casts, which would need to be cut off each time, and then having to use a different removable brace, this patient was able to use the same multifunctional orthosis device for the entire duration of management of the patient's 2nd metacarpal fracture necessitating a "radial gutter" configuration for treatment, reducing the doctor's office inventory both of traditional cast and brace supplies and even of multifunctional orthosis devices since one device can advantageously be used for such applications on either the right or left hand and in both ulnar and radial configurations as particularly enabled by the optional thumb hole opening.

Aspects of the present specification may also be described as follows:

1. An orthosis device comprising: a substantially rigid thermo-formable substrate having a substrate profile defined by a substrate top edge, an opposite substrate bottom edge, and opposite substrate side edges interconnecting the substrate top and bottom edges, the substrate profile being substantially symmetrical about a centerline thereof; whereby the device becomes moldable when activated by a forming temperature above ambient, and the symmetry of the substrate enables the device to be used in both left hand and right hand applications.

2. The device of embodiment 1 wherein the substrate comprises a main body portion and opposite lower wing portions partially defining the substrate bottom and side edges, each wing portion being joined to the body portion along a substantially angled hinge.

3. The device of embodiment 2 wherein the main body portion and the wing portions are integral and each hinge is configured as a living hinge.

4. The device of embodiment 2 or embodiment 3 further comprising a fastener strip formed along each hinge opposite the pad.

5. The device of any of embodiments 2-4 wherein the substrate further comprises one or more trim lines formed within at least one of the main body portion and the wing portions, the trim lines being substantially parallel to and offset from the bottom edge of the substrate.

6. The device of any of embodiments 1-5 further comprising a liner pad coupled to the substrate in a substantially abutting arrangement, the pad having a pad profile defined by a pad top edge, an opposite pad bottom edge, and opposite pad side edges interconnecting the pad top and bottom edges, the pad profile substantially corresponding to the substrate profile.

7. The device of embodiment 6 wherein: the main body portion comprises an upper stabilizer region; and the pad comprises an upper finger wrap tab extending outwardly from a pad side edge and partially defining the pad top edge.

8. The device of embodiment 7 further comprising a first fastener assembly formed on the finger wrap tab.

9. The device of embodiment 7 or embodiment 8 wherein the pad further comprises a finger sleeve formed on an inner surface thereof and configured for selective receipt of one or more fingers of a patient during use of the device, the finger sleeve cooperating with the finger wrap tab to enable operation of the stabilizer region of the substrate.

10. The device of any of embodiments 1-9 wherein the substrate comprises a central portion formed having a substrate thumb hole and a selectively removable thumb hole cover installed within the substrate thumb hole, whereby the thumb hole cover may be removed and a thumb of a patient inserted through the substrate thumb hole during use of the device in a radial gutter application.

11. The device of embodiment 10 wherein a liner pad is coupled to the substrate in a substantially abutting arrangement, the pad comprising a pad thumb hole substantially corresponding to the substrate thumb hole.

12. The device of embodiment 11 wherein the pad further comprises a padding insert having a thumb hole flap configured to selectively overlie the pad thumb hole.

13. The device of any of embodiments 10-12 further comprising a thumb spica having a base configured to seat on the central portion of the substrate with an extension protruding at an angle therefrom, the thumb spica cooperating with the device to stabilize the thumb in a radial gutter application.

14. The device of any of embodiments 1-13 wherein a liner pad is coupled to the substrate in a substantially abutting arrangement, the pad comprising an upper finger wrap tab extending outwardly therefrom and having a first fastener assembly formed on the finger wrap tab, the pad further comprising a lower second fastener assembly.

15. The device of any of embodiments 1-14 wherein the substrate further comprises a plurality of apertures.

16. The device of any of embodiments 1-15 wherein the substrate is formed of polycaprolactone.

17. An orthosis device comprising a substantially rigid thermo-formable substrate having a main body portion and opposite lower wing portions, each wing portion being joined to the body portion along a substantially angled hinge, the substrate being substantially symmetrical about a centerline thereof substantially along the main body portion.

18. The device of embodiment 17 wherein the main body portion and the wing portions are integral and each hinge is configured as a living hinge.

19. The device of embodiment 17 or embodiment 18 wherein the substrate further comprises a central portion formed having a substrate thumb hole and a selectively removable thumb hole cover installed within the substrate thumb hole, whereby the thumb hole cover may be removed and a thumb of a patient inserted through the substrate thumb hole during use of the device in a radial gutter application.

20. The device of embodiment 19 further comprising a liner pad coupled to the substrate in a substantially abutting arrangement, the pad having a pad thumb hole substantially corresponding to the substrate thumb hole.

21. An orthosis device comprising a substantially rigid thermo-formable substrate having a main body portion and a central portion formed having a substrate thumb hole and a selectively removable thumb hole cover installed within the substrate thumb hole, the substrate being substantially symmetrical about a centerline thereof substantially along the main body portion, whereby the thumb hole cover may be removed and a thumb of a patient inserted through the substrate thumb hole during use of the device in a radial gutter application.

22. The device of embodiment 21 further comprising a liner pad coupled to the substrate in a substantially abutting arrangement, the pad having a pad thumb hole substantially corresponding to the substrate thumb hole.

23. The device of embodiment 21 or embodiment 22 wherein the substrate further comprises a main body portion and opposite lower wing portions, each wing portion being joined to the body portion along a substantially angled hinge.

24. An orthosis device comprising: a substantially rigid thermo-formable substrate having a substrate profile defined by a substrate top edge, an opposite substrate bottom edge, and opposite substrate side edges interconnecting the substrate top and bottom edges, the substrate profile being substantially symmetrical about a centerline thereof, the substrate having a main body portion and opposite lower wing portions, each wing portion being joined to the body portion along a substantially angled hinge, the substrate further having a central portion formed having a substrate thumb hole and a selectively removable thumb hole cover installed within the substrate thumb hole; and a liner pad coupled to the substrate in a substantially abutting arrangement, the pad having a pad profile defined by a pad top edge, an opposite pad bottom edge, and opposite pad side edges interconnecting the pad top and bottom edges, the pad profile substantially corresponding to the substrate profile, the pad further having a pad thumb hole substantially corresponding to the substrate thumb hole; whereby the device becomes moldable when activated by a forming temperature above ambient, and the symmetry of the substrate enables the device to be used in both left hand and right hand applications; and whereby the thumb hole cover may be removed and a thumb of a patient inserted through the substrate thumb hole during use of the device in a radial gutter application, such that the device may be used in both radial and ulnar applications.

In closing, regarding the exemplary embodiments of the present invention as shown and described herein, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular apparatus, methodology, configuration, size, shape, material of construction, protocol, etc., described herein, but may include any such technology now known or later developed without departing from the spirit and scope of the specification. As such, various modifications or changes to or alternative configurations of the disclosed subject matter can be made in accordance with the teachings herein without departing from the spirit and scope of the present specification. Lastly, the terminology used herein is for the purpose of describing particular embodiments only, and is not intended to limit the scope of the present invention. Accordingly, the present invention is not limited to that precisely as shown and described.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. An orthosis device comprising:
a substantially rigid thermo-formable substrate having a substrate profile defined by a substrate top edge, an opposite substrate bottom edge, and opposite substrate side edges interconnecting the substrate top and bottom edges, the substrate profile being substantially symmetrical about a centerline thereof, the centerline being centered vertically along the substrate from the substrate top edge to the substrate bottom edge, wherein the substrate comprises a main body portion and opposite lower wing portions partially defining the substrate bottom edge and the respective substrate side edges, each of the lower wing portions being joined to the main body portion along a respective hinge that is formed at an angle relative to the centerline so as to intersect both the substrate bottom edge and the respective substrate side edge;
whereby the device becomes moldable when activated by a forming temperature above ambient, and the symmetry of the substrate enables the device to be used in both left hand and right hand applications.

2. The device of claim 1 further comprising a liner pad coupled to the substrate in a substantially abutting arrangement, the liner pad having a pad profile defined by a pad top edge, an opposite pad bottom edge, and opposite pad side edges interconnecting the pad top and bottom edges, the pad profile substantially corresponding to the substrate profile.

3. The device of claim 2 wherein:
the main body portion comprises an upper stabilizer region; and
the liner pad comprises an upper finger wrap tab extending outwardly from a pad side edge and partially defining the pad top edge.

4. The device of claim 3 further comprising a first fastener assembly formed on the upper finger wrap tab.

5. The device of claim 3 wherein the liner pad further comprises a finger sleeve formed on an inner surface thereof and configured for selective receipt of one or more fingers of a patient during use of the device, the finger sleeve cooperating with the upper finger wrap tab to enable operation of the stabilizer region of the substrate.

6. The device of claim 1 wherein the substrate comprises a central portion formed having a substrate thumb hole and a selectively removable thumb hole cover installed within the substrate thumb hole, and wherein the thumb hole cover is configured to be selectively retained within the substrate thumb hole to provide a substantially continuous support surface for a hand of a patient during use of the device in an ulnar gutter application and to be selectively removed from the substrate thumb hole to allow a thumb of a patient to be inserted through the substrate thumb hole during use of the device in a radial gutter application.

7. The device of claim 6 wherein a liner pad is coupled to the substrate in a substantially abutting arrangement, the liner pad comprising a pad thumb hole substantially corresponding to the substrate thumb hole.

8. The device of claim 7 wherein the liner pad further comprises a padding insert having a thumb hole flap configured to selectively overlie the pad thumb hole.

9. The device of claim 6 further comprising a thumb spica having a base configured to seat on the central portion of the substrate with an extension protruding at an angle therefrom, the thumb spica configured to cooperate with the device to stabilize a thumb of a patient in a radial gutter application.

10. The device of claim 1 wherein the main body portion and the lower wing portions are integral and each hinge is configured as a living hinge.

11. The device of claim 10 further comprising a fastener strip formed along each hinge.

12. The device of claim 1 wherein each hinge defines a hinge angle relative to the centerline from ten to thirty degrees (10-30°).

13. The device of claim 1 wherein the substrate further comprises one or more trim lines formed within at least one of the main body portion and the lower wing portions, the trim lines being substantially parallel to and offset from the bottom edge of the substrate.

14. The device of claim 1 wherein a liner pad is coupled to the substrate in a substantially abutting arrangement, the liner pad comprising an upper finger wrap tab extending outwardly therefrom and having a first fastener assembly formed on the upper finger wrap tab, the liner pad further comprising a lower second fastener assembly.

15. The device of claim 1 wherein the substrate further comprises a plurality of apertures.

16. The device of claim 1 wherein the substrate is formed of polycaprolactone.

17. An orthosis device comprising a substantially rigid thermo-formable substrate having a substrate top edge, a substrate bottom edge, and opposite substrate side edges interconnecting the substrate top and bottom edges and further having a main body portion and opposite lower wing portions, the substrate having a centerline thereof substantially vertically along the main body portion, each of the lower wing portions being joined to the main body portion along a hinge, the hinge defining a fixed hinge axis about which the respective lower wing portion pivots relative to the main body portion, the hinge axis formed at an angle relative to the centerline so as to intersect both the substrate bottom edge and the respective substrate side edge, whereby movement of the lower wing portions about the hinges to positions out of plane relative to the body portion facilitates opening of the orthosis device.

18. The device of claim 17 wherein the substrate further comprises a central portion formed having a substrate thumb hole and a selectively removable thumb hole cover installed within the substrate thumb hole, and wherein the thumb hole cover is configured to be selectively retained within the substrate thumb hole to provide a substantially continuous support surface for a hand of a patient during use of the device in an ulnar gutter application and to be selectively removed from the substrate thumb hole to allow a thumb of a patient to be inserted through the substrate thumb hole during use of the device in a radial gutter application.

19. The device of claim 18 further comprising a liner pad coupled to the substrate in a substantially abutting arrangement, the liner pad having a pad thumb hole substantially corresponding to the substrate thumb hole.

20. The device of claim 17 wherein the main body portion and the lower wing portions are integral and each hinge is configured as a living hinge.

21. An orthosis device comprising a substantially rigid thermo-formable substrate having a main body portion and a central portion formed having a substrate thumb hole and a selectively removable thumb hole cover installed within the substrate thumb hole, wherein the thumb hole cover is configured to be selectively retained within the substrate thumb hole to provide a substantially continuous support surface for a hand of a patient during use of the device in an ulnar gutter application and to be selectively removed from the substrate thumb hole to allow a thumb of a patient to be inserted through the substrate thumb hole during use of the device in a radial gutter application.

22. The device of claim 21 further comprising a liner pad coupled to the substrate in a substantially abutting arrangement, the liner pad having a pad thumb hole substantially corresponding to the substrate thumb hole.

23. The device of claim 21 wherein the substrate further comprises opposite lower wing portions, each of the lower wing portions being joined to the main body portion along a substantially angled hinge.

24. An orthosis device comprising:
a substantially rigid thermo-formable substrate having a substrate profile defined by a substrate top edge, an opposite substrate bottom edge, and opposite substrate side edges interconnecting the substrate top and bottom edges, the substrate profile being substantially symmetrical about a centerline thereof, the centerline being centered vertically along the substrate from the substrate top edge to the substrate bottom edge, the substrate having a main body portion and opposite lower wing portions, each of the lower wing portions being joined to the main body portion along a substantially angled hinge relative to the centerline, the substrate further having a central portion formed having a substrate thumb hole and a selectively removable thumb hole cover installed within the substrate thumb hole; and
a liner pad coupled to the substrate in a substantially abutting arrangement, the liner pad having a pad profile defined by a pad top edge, an opposite pad bottom edge, and opposite pad side edges interconnecting the pad top and bottom edges, the pad profile substantially corresponding to the substrate profile, the liner pad further having a pad thumb hole substantially corresponding to the substrate thumb hole;
wherein the device becomes moldable when activated by a forming temperature above ambient, and the symmetry of the substrate enables the device to be used in both left hand and right hand applications; and
wherein the thumb hole cover is configured to be selectively retained within the substrate thumb hole to provide a substantially continuous support surface for a hand of a patient during use of the device in an ulnar gutter application and to be selectively removed from the substrate thumb hole to allow a thumb of a patient to be inserted through the substrate thumb hole during use of the device in a radial gutter application, such that the device may be used in both radial and ulnar gutter applications.

* * * * *